(12) United States Patent
Ume et al.

(10) Patent No.: US 9,201,046 B2
(45) Date of Patent: Dec. 1, 2015

(54) WELD ANALYSIS USING LASER GENERATED NARROWBAND LAMB WAVES

(75) Inventors: Ifeanyi Charles Ume, Atlanta, GA (US); Tsun-Yen Wu, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 13/883,304

(22) PCT Filed: Aug. 30, 2011

(86) PCT No.: PCT/US2011/049787
§ 371 (c)(1),
(2), (4) Date: May 3, 2013

(87) PCT Pub. No.: WO2013/032450
PCT Pub. Date: Mar. 7, 2013

(65) Prior Publication Data
US 2014/0172399 A1    Jun. 19, 2014

(51) Int. Cl.
*G01N 29/52*    (2006.01)
*G01N 29/04*    (2006.01)
*G01N 29/24*    (2006.01)
(Continued)

(52) U.S. Cl.
CPC ............... *G01N 29/041* (2013.01); *B23K 9/16* (2013.01); *B23K 9/23* (2013.01); *B23K 31/125* (2013.01); *G01N 29/2412* (2013.01); *G01N 29/2418* (2013.01); *G01N 29/343* (2013.01); *G01N 29/4418* (2013.01); *G01N 29/4472* (2013.01); *G01N 29/46* (2013.01); *B23K 2201/18* (2013.01); *B23K 2203/04* (2013.01); *G01N 2291/0427* (2013.01); *G01N 2291/267* (2013.01)

(58) Field of Classification Search
CPC ............ G01N 29/46; G01N 29/2418; G01N 2291/0422; G01N 29/2412; G01N 29/4463; G01N 29/449
USPC ................... 73/643, 655, 659, 602
See application file for complete search history.

(56) References Cited

U.S. PATENT DOCUMENTS 4,911,014 A * 3/1990 Lund et al. ............ 73/602
5,439,157 A    8/1995 Geier et al.
(Continued)

OTHER PUBLICATIONS

Dixon et al., A Laser-EMAT System for Ultrasonic Weld Inspection, Ultrasonics, vol. 37, No. 4, Apr. 1999, pp. 273-281.*
(Continued)

*Primary Examiner* — Lauran Martin
*Assistant Examiner* — Rose M Miller
(74) *Attorney, Agent, or Firm* — Troutman Sanders LLP; Ryan A. Schneider; Benjamin C. Wiles

(57) ABSTRACT

A system and method for measuring various weld characteristics is presented. The system and method can comprise a means to measure penetration depth of butt welds in thin plates, for example, using laser generated ultrasounds. Superimposed line sources (SLS) can be used to generate narrowband ultrasounds. A signal processing procedure that combines wavenumber-frequency (k-ω) domain filtering and synthetic phase tuning (SPT) is used to reduce the complexity of Lamb wave signals. The reflection coefficients for different wavelengths corresponding to each wave mode can be calculated. Regression analysis that can include stepwise regression and corrected Akaike's information criterion (AIC) can be performed to build prediction models that use the reflection coefficients as predictors.

19 Claims, 21 Drawing Sheets

(51) Int. Cl.
*G01N 29/44* (2006.01)
*G01N 29/46* (2006.01)
*G01N 29/34* (2006.01)
*B23K 9/16* (2006.01)
*B23K 9/23* (2006.01)
*B23K 31/12* (2006.01)

(56) References Cited

U.S. PATENT DOCUMENTS

| | | | |
|---|---|---|---|
| 5,608,166 A | 3/1997 | Monchalin et al. | |
| 6,397,679 B1 | 6/2002 | Sadok et al. | |
| 7,278,315 B1 | 10/2007 | Klein et al. | |
| 2003/0234239 A1 | 12/2003 | Lee et al. | |
| 2004/0003662 A1* | 1/2004 | Kenderian et al. | 73/579 |
| 2005/0267703 A1 | 12/2005 | Bondurant et al. | |
| 2008/0072674 A1* | 3/2008 | Ume et al. | 73/627 |
| 2008/0229832 A1 | 9/2008 | Huang et al. | |
| 2009/0122028 A1 | 5/2009 | Ing | |
| 2009/0301198 A1 | 12/2009 | Sohn et al. | |
| 2010/0319456 A1* | 12/2010 | Ume et al. | 73/622 |
| 2011/0023609 A1* | 2/2011 | Ume et al. | 73/600 |
| 2011/0023610 A1 | 2/2011 | Ume et al. | |
| 2011/0108181 A1 | 5/2011 | Cal et al. | |
| 2013/0047731 A1* | 2/2013 | Ume et al. | 73/643 |
| 2013/0228560 A1* | 9/2013 | Ume et al. | 219/137 R |

OTHER PUBLICATIONS

The International Search Report and Written Opinion dated Dec. 16, 2011.

The International Preliminary Report on Patentability dated Mar. 13, 2014.

Extended European Search Report in related Application No. EP11871495.5 dated Mar. 23, 2015.

* cited by examiner

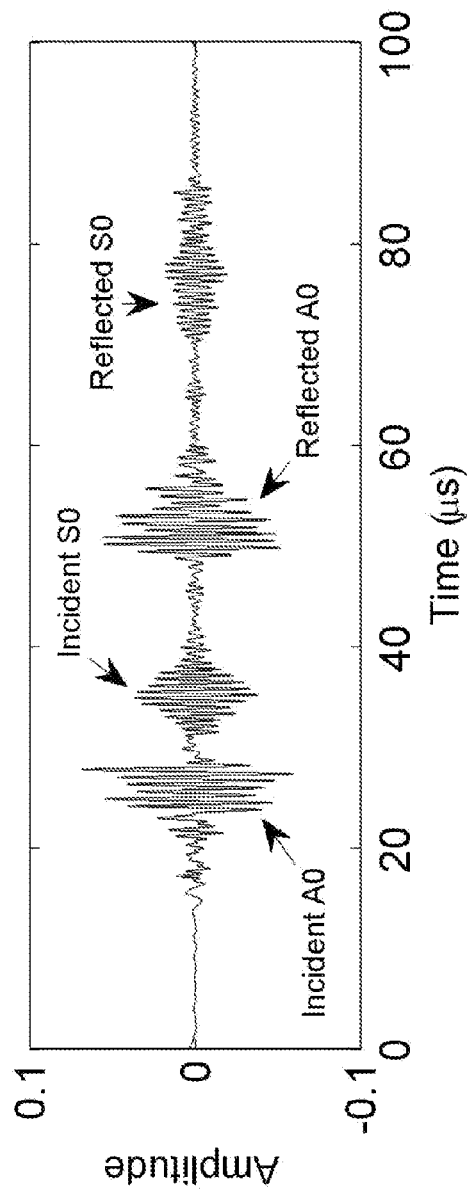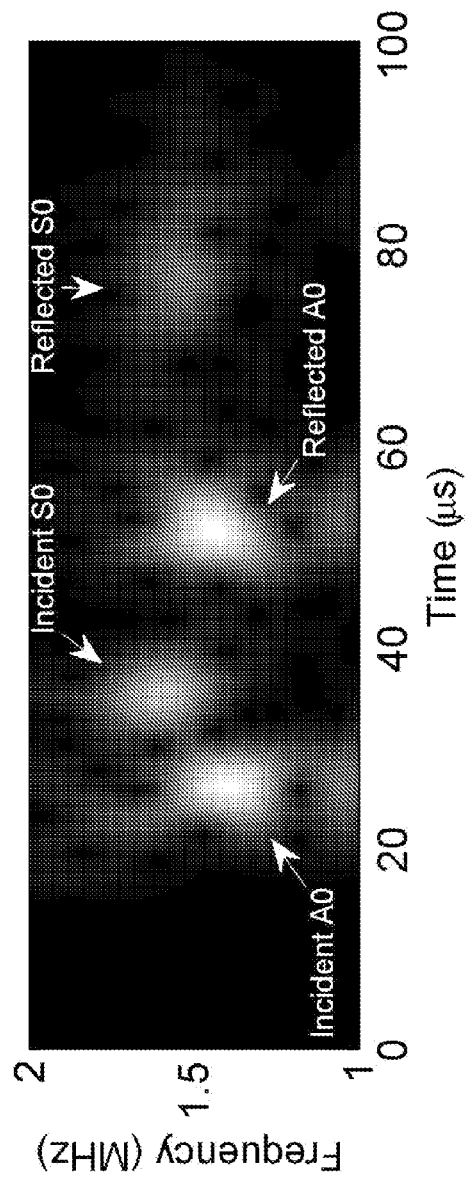
Fig. 8a
Fig. 8b

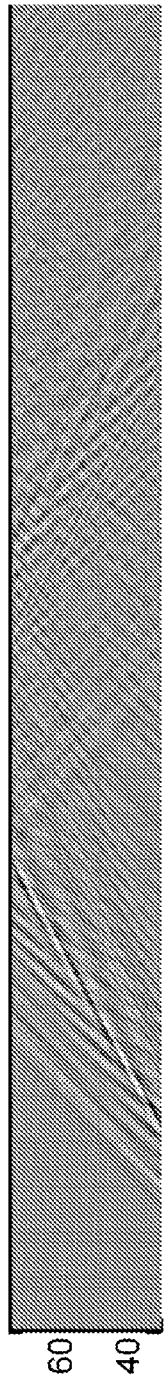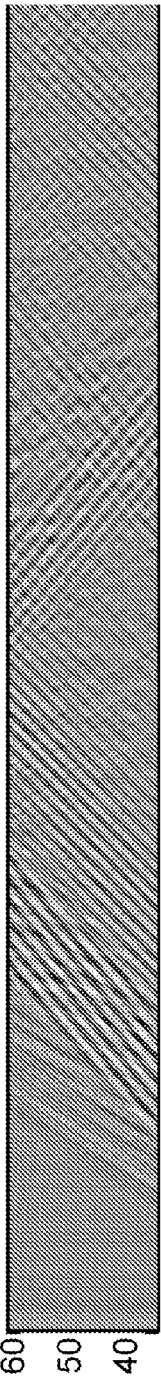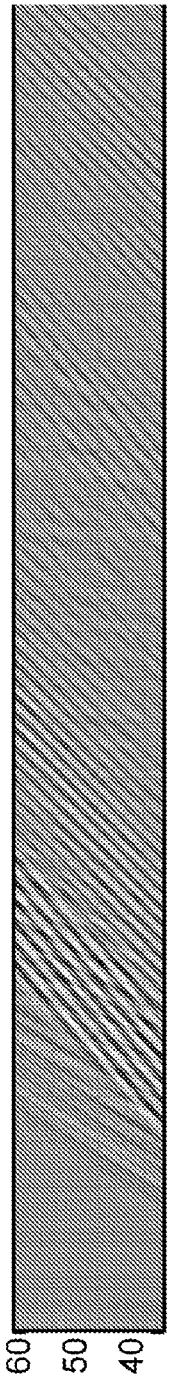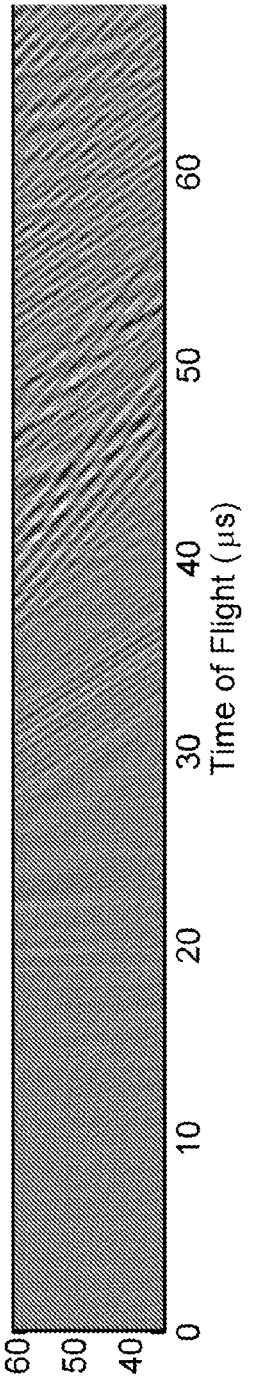
Fig. 15a
Fig. 15b
Fig. 15c
Fig. 15d

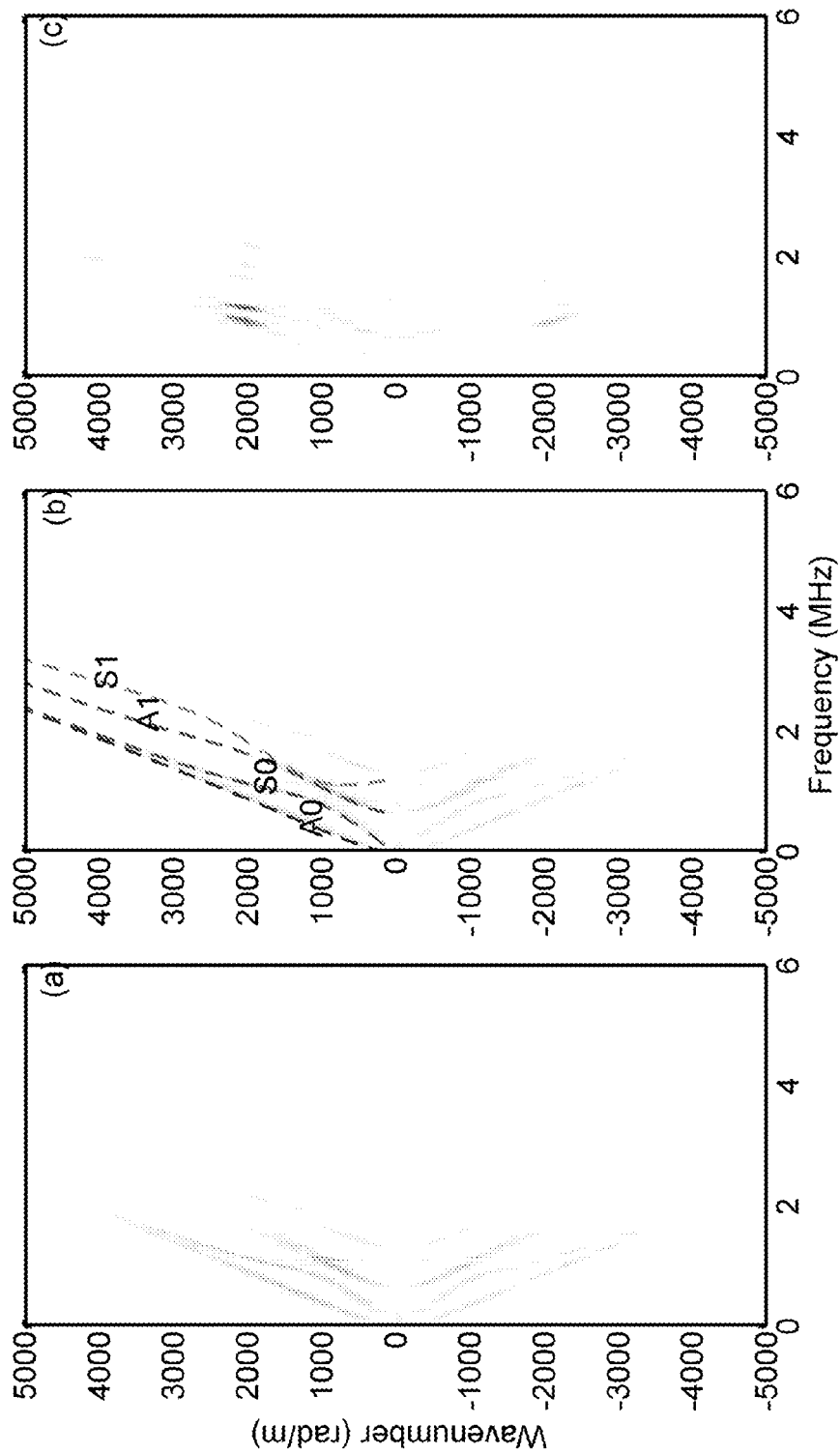

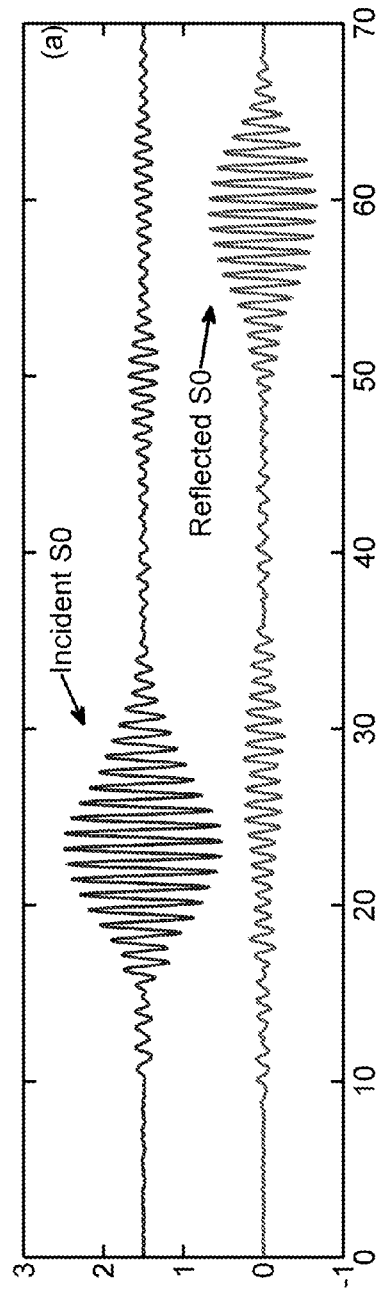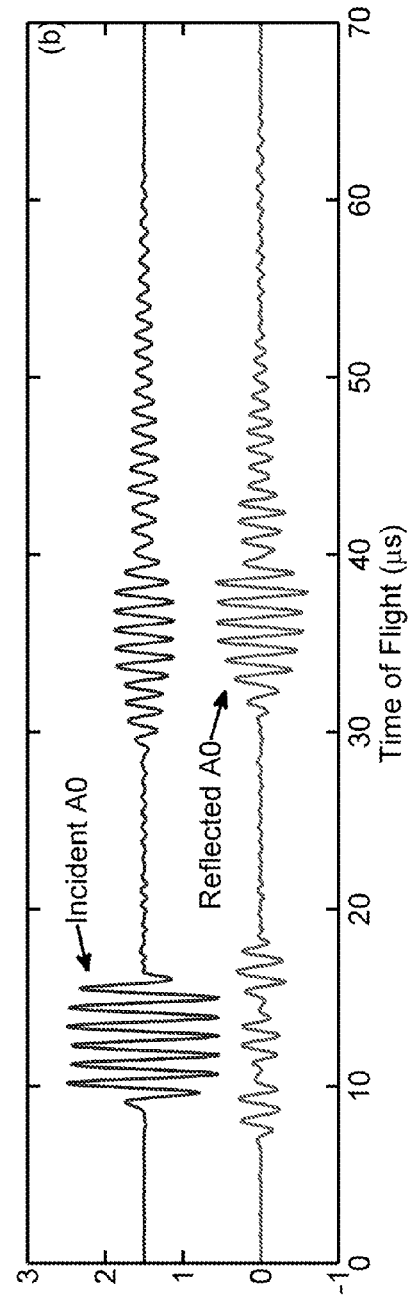
Fig. 17a
Fig. 17b

WELD ANALYSIS USING LASER GENERATED NARROWBAND LAMB WAVES

CROSS-REFERENCE TO RELATED APPLICATIONS

This application is a US National Stage under 35 U.S.C. §371 of International Application No. PCT/US2011/049787, filed Aug. 30, 2011, which is fully incorporated herein by reference as if set forth below.

BACKGROUND OF THE INVENTION

1. Field of the Invention

Embodiments of the present invention relates to a system and method for generating narrowband Lamb waves for use in, for example and not limitation, non-destructive testing. Specifically, embodiments of the present invention relate to the non-contact generation of Lamb waves in thin plates using laser beams and software analysis to analyze weld parameters including, but not limited to, weld penetration.

2. Background of Related Art

Butt joint welding is an essential process of joining parts in many industries. The schematic of cross section of a butt weld is shown in FIG. 1, which depicts a variety of weld dimensions including penetration depth (PD), reinforcement height (RH) and bead width (BW). Among them, PD is an important geometric parameter that indicates weld quality and is used as a key quality control quantity. The evaluation of PD in butt welds in thin plates, therefore, has many practical applications. Conventionally, cutcheck, i.e., physically cutting the sample across the weld, has been widely used to monitor weld quality. This procedure, however, is time-consuming, destructive, and wasteful. In addition, automated inspection using cutcheck is not possible.

For at least the preceding reasons, it is desirable to perform non-destructive testing ("NDT") on a variety of materials to detect and locate, for example and not limitation, material defects, manufacturing defects, and weld quality. As a result, considerable resources have been invested to develop NDT methods such as, among other things, ultrasonic inspection, radiography, thermography, and eddy current inspection.

Ultrasonic inspection techniques have gained greater acceptance for a variety of purposes in recent years. It is one of the major techniques used, for example, for inspection of welds in structures. Conventionally, contact piezoelectric transducers (PZTs) have been used to generate and receive ultrasounds during offline, as opposed to real-time, sample inspection. Due to the need for liquid couplants between the PZTs and the sample, however, this method is not suitable for automated real-time inspection during manufacture.

Non-contact ultrasonic sensing, on the other hand, has the potential to detect defects and discontinuities in real time. Using laser generated ultrasounds and an electromagnetic acoustic transducer (EMAT) receiver, for example, is one method suitable for both offline and real-time sample quality monitoring. Nanosecond pulse width lasers such as, for example, Q-switched Nd:YAG lasers can be used to generate ultrasound.

In use, a high energy, very short duration pulse from the laser induces a rapid increase in the local temperature of the sample. The heated region expands thermoelastically and then slowly contracts when the laser pulse is momentarily shut off. The rapid expansion and slower contraction creates ultrasounds which propagate through the sample. In addition to the thermoelastic effect, ablation can occur if the energy of the laser pulse is increased to the point that some portion of the surface evaporates. The ultrasounds generated in the ablation regime are much stronger than those generated in the thermoelastic regime, though the latter is generally preferred for true NDT.

Conventionally, a laser or a laser phased array system has been used to generate ultrasounds (i.e., bulk waves) to measure various characteristics in thick structures (e.g., weld penetration). A Time of flight diffraction (TOFD) technique can be used to evaluate, for example, material defects or weld characteristics. By measuring the arrival time of an ultrasonic signal, for example, various characteristics of weld such a penetration depth can be measured.

When the thickness of the sample approaches the wavelength of the ultrasonic wave, however, this method no longer provides accurate data. For thin materials, ultrasonic waves give way to Lamb waves, which exhibit very different characteristics compared to the bulk waves that travel in thick structures. Lamb waves travel through the cross section of the structure, are dispersive, and their traveling speeds are dependent on their frequencies. Lamb waves are widely used in structural integrity inspection and defect detection in thin structures because of their potentials to inspect large area and their sensitivity to a variety of damage types.

The use of lasers to generate Lamb waves is beneficial due to its noncontact nature. Laser generated ultrasound is broadband in nature, however, and this, combined with the dispersive nature of Lamb waves, makes signal processing complicated. To simplify signal processing in thin structures, therefore, narrowband Lamb waves are desirable.

Conventionally, this has been achieved using spatial array illumination sources produced by, for example, shadow masks, optical diffraction gratings, multiple lasers, interference patterns, and lenticular arrays. Shadow masks, depicted in FIG. 3a, are economical, fairly effective and easy to implement (hereinafter referred to as "pattern source"), but they are not flexible and have several disadvantages. These include, but are not limited to, the need to fabricate different masks for each different wavelength of interest, the absorption of a substantial amount of energy by the mask, and the inability to practically manufacture masks with very small spacing. In addition, because the masks must be manually changed for each separate wavelength, experimental setup for masks for a large number of wavelengths can be impractical.

With respect to the analysis of welds in particular, the relationship between the reflection coefficients of Lamb wave modes and geometry of notches with varying width or depth in thin plates has been investigated. Some previous methods include the boundary element method and the finite element method to study reflection coefficients of fundamental $A_0$ and $S_0$ Lamb wave modes from a notch. Previous investigation has shown that reflection coefficients of Lamb waves are not only dependent on the geometry of the notches, but also on the wavelengths of Lamb waves. The Study of guided waves traveling in elastic plates with Gaussian section variation showed that waves can be trapped in the Gaussian domain depending on the incident mode and on the Gaussian maximum height.

The geometry of a butt weld can be approximated as a plate with Gaussian section variation and a notch. No analytical solutions or models can be found in the literature, however, to describe how Lamb waves propagate in this kind of structure. The problem is further complicated by the existence of the material interfaces between the weld bead and the base material. Prior to the development of embodiments of the present invention, all that was known is that the reflected waves contain information regarding weld dimensions. Utilizing this information remained a mystery.

What is needed, therefore, is a system and method ("system") for efficiently creating narrowband Lamb waves using a focused energy source (e.g., one or more laser sources). The system should retain the non-contact benefits of conventional pattern source methods, but provide improved flexibility and efficiency. The system should reduce wave complexity using various mathematical methods to enable analysis of wave behavior for NDT of, for example, butt welds in thin plates. It is to such a system and method that embodiments of the present invention are primarily directed.

BRIEF SUMMARY OF THE INVENTION

Embodiments of the present invention can comprise a system and method for providing laser generated, narrowband Lamb waves utilizing various techniques, including, but not limited to, superimposed line sources, Fourier transforms, and wavelet transforms. The system and method can generate narrowband Lamb waves with a dominant wavelength by superimposing signals of line sources at the pitch corresponding to the desired wavelength. The superposition can be performed in software after data are collected to permit flexibility in the wavelength selection. Selecting the dominant wavelength in signals can reduce signal complexity and the speeds and frequencies of wave modes with the selected wavelength can be determined using dispersion curves. One or more additional techniques can be used to further reduce the complexity of the signals. The system and method can be used, for example, for defect detection in thin plates.

Embodiments of the present invention can comprise, for example, a system for generating narrow band Lamb waves in a sample. The system can comprise a concentrated energy source, such as a pulse laser, for creating localized heating in the sample. The localized heating (and cooling) from the pulse laser can cause ultrasonic waves in the sample. An ultrasound receiver, such as, for example and not limitation, an electromagnetic acoustic transducer, can be used to detect the ultrasonic waves. In some embodiments, after each laser firing a linear stage can move the sample a first predetermined distance. The predetermined distance is preferably smaller than a desired wavelength for analysis. In some embodiments, the predetermined distance can be decided by the minimum difference in the wavelengths of interest. In some embodiments, a computer readable medium can be used to store one or more signals generated by the ultrasound receiver.

In some embodiments, the concentrated energy source can be fired through a cylindrical lens to convert the concentrated energy from the pulsed width laser to a line source pattern. In a preferred embodiment, a lens, such as, for example and not limitation, a concave lens, can be provided to make the laser beam collimated. The system can further comprise a computer processor for superimposing the one or more signals received by the ultrasound receiver to reduce the complexity of the signals. In some embodiments, the computer processor can further reduce the complexity of the signals using, for example, a two-dimensional Fourier transform or a complex Morlet mother wavelet.

Embodiments of the present invention can also comprise a method for generating narrow band Lamb waves in a sample. The method can comprise (1) activating a pulsed, concentrated energy source to create ultrasonic waves in the sample; (2) receiving the ultrasound waves with an ultrasound receiver; (3) storing the signal generated by the ultrasound receiver on a computer readable medium; (4) moving the sample a first predetermined distance; and repeating steps 1-4 until the sample has moved a second predetermined distance.

In some embodiments, the method can further comprise retrieving the signals stored on the computer readable medium and superimposing the signals that correspond to a first wavelength to create an artificial pattern source. The artificial pattern source can also be stored on the computer readable medium. In some embodiments, the method can further comprise retrieving the artificial pattern source from the computer readable medium and reducing the complexity of the pattern source using a two-dimensional Fourier transform. The simplified pattern source can also be stored on the computer readable medium. In some embodiments, the method can further comprise retrieving the artificial pattern source from the computer readable medium and reducing the complexity of the pattern source using a complex Morlet mother wavelet. In other embodiments, other types of wavelet analysis including but not limited to, other mother wavelets can be used.

These and other objects, features and advantages of the present invention will become more apparent upon reading the following specification in conjunction with the accompanying drawing figures.

BRIEF DESCRIPTION OF THE DRAWINGS

FIGS. 8a and 8b compare graphs representing symmetric and antisymmetric mode signals interpreted in the time-amplitude and time-frequency, respectively, in accordance with some embodiments of the present invention.

FIGS. 15a-15d depict more wave forms of decreasing complexity as they are processed using embodiments of the present invention.

FIGS. 16a-16c depict more wave forms that have been simplified using a two-dimensional Fourier transform, in accordance with some embodiments of the present invention.

FIGS. 17a and 17b depict graphs representing signals interpreted in the time-amplitude domain, in accordance with some embodiments of the present invention.

DETAILED DESCRIPTION OF THE INVENTION

Figure 1:
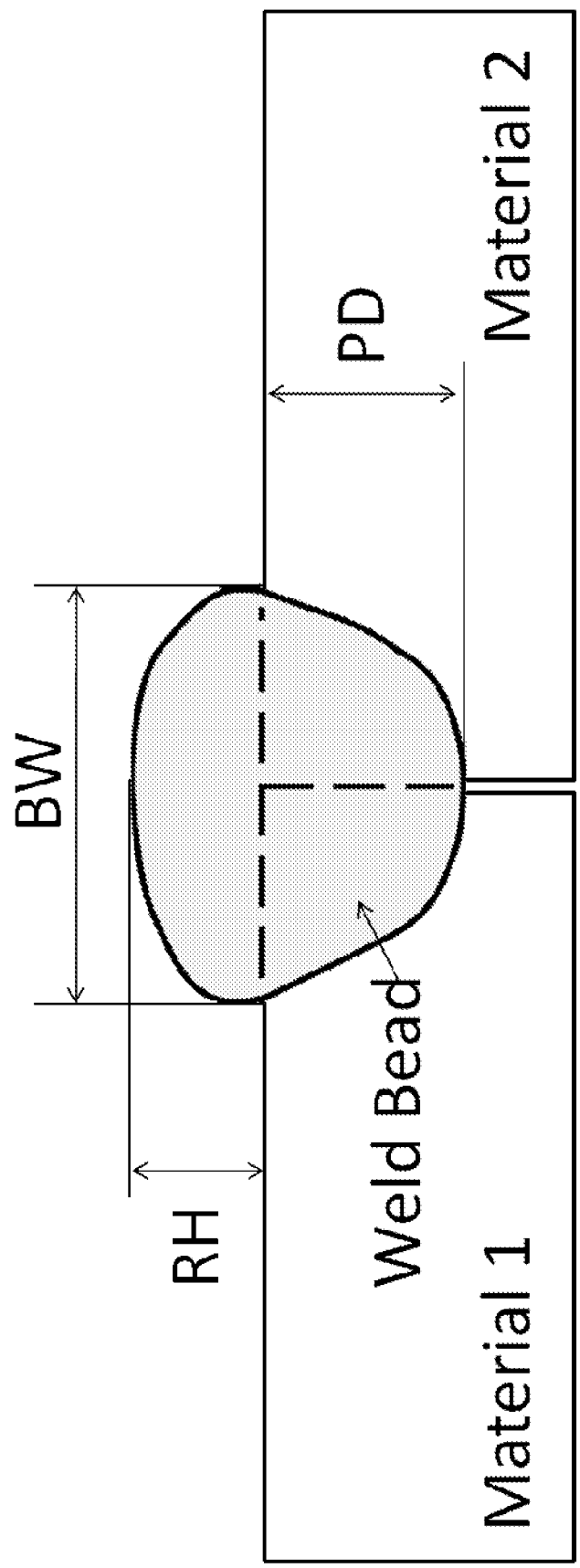
FIG. 1 is a diagram of a conventional butt weld joining two pieces of metal.

Embodiments of the present invention relate generally to a system for generating narrowband Lamb waves using one or more lasers, and specifically to a system and method for generating narrowband Lamb waves in thin materials for conducting non-destructive testing ("NDT") and analysis of welds. The system improves upon conventional methods by providing, among other things, additional energy efficiency and wavelength flexibility. The system can use one or more lasers to generate broadband waves in the sample material. The signals generated therefrom can be processed to simplify and isolate the desired wavelengths to determine speed and frequency. The knowledge of speeds and frequencies of narrowband Lamb wave modes permits identification and time-of-flight analysis of each Lamb wave mode in applications. This information can be used to develop prediction models for various weld parameters to facilitate efficient weld analysis without the use of conventional cutchecks.

To simplify and clarify explanation, the system is described below as a system for NDT and analysis of welds in thin plates. One skilled in the art will recognize, however, that the invention is not so limited. The system can also be deployed for NDT and analysis in, for example, thick plates or where large area analysis provided by Lamb waves is desirable. The ability of Lamb waves to travel long distances can be useful to enable the NDT of large areas to improve production speeds and reduce cost. The system can also be used for analysis of other types of joints including, but not limited to, glued joints.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed, for example, after the time of the development of the invention. Any dimensions listed in the various drawings are for illustrative purposes only and are not intended to be limiting. Other dimensions and proportions are contemplated and intended to be included within the scope of the invention.

As mentioned above, several problems exist with laser generated ultrasound generated using conventional techniques, such as the shadow mask technique. Problems include, but are not limited to, loss of laser energy at the mask, difficulty in manufacturing the masks, and difficulty in changing the masks during use. These line sources nonetheless provided several advantages such as, for example and not limitation, enabling non-contact generation of ultrasonic waves. Non-contact testing can enable, for example, real-time NDT of materials during manufacture. Real-time NDT can, for example, quickly identify material flaws to enable manufacturing adjustments to be made in a timely manner, which can reduce downtime, increase production, and reduce material waste and cost.

To this end, embodiments of the present invention can comprise a method utilizing superimposed line sources (SLS). The method can generate narrowband Lamb waves with a dominant wavelength by superimposing signals from line sources at a pitch corresponding to a desired wavelength. The superposition can be performed in software so that the desired wavelength can be selected after testing. By selecting the dominant wavelength in the signals, the complexity of laser generated broadband signals can be greatly reduced and the speeds and frequencies of traveling ultrasounds at the selected wavelength can be easily determined using standard dispersion curves (i.e., graphs that show relationships between wave velocity, wavelength, and frequency in dispersive systems). The knowledge of speeds and frequencies of narrowband Lamb wave can enable the identification and time-of-flight analysis for each Lamb wave mode.

After narrowband Lamb waves have been created using SLS, a signal processing procedure that can include wavenumber-frequency (k-ω) domain filtering and continuous wavelet transform (CWT), which can be used to help identify wave packets of the zero order anti-symmetric mode ("$A_0$") and the zero order symmetrical mode ("$S_0$") Lamb wave modes. This, in turn, can be used to identify, for example and not limitation, the location of a material defect in a sample.

Laser Generation of Ultrasound

As mentioned above, the use of pulsed lasers to generate ultrasound is useful because of its noncontact nature. Unlike traditional contact piezoelectric transducers (PZTs), for example, laser generation does not require couplants on the surfaces of samples. This makes it suitable for use in, for example, automated inspection during production. When the laser irradiates the surface of the sample, the high energy and short duration of each pulse induces a quick increase in local temperature. The heated region thermoelastically expands and then slowly contracts when the laser is switched off. The rapid expansion and slower contraction create broadband ultrasound waves propagating in the sample.

Figure 3A:
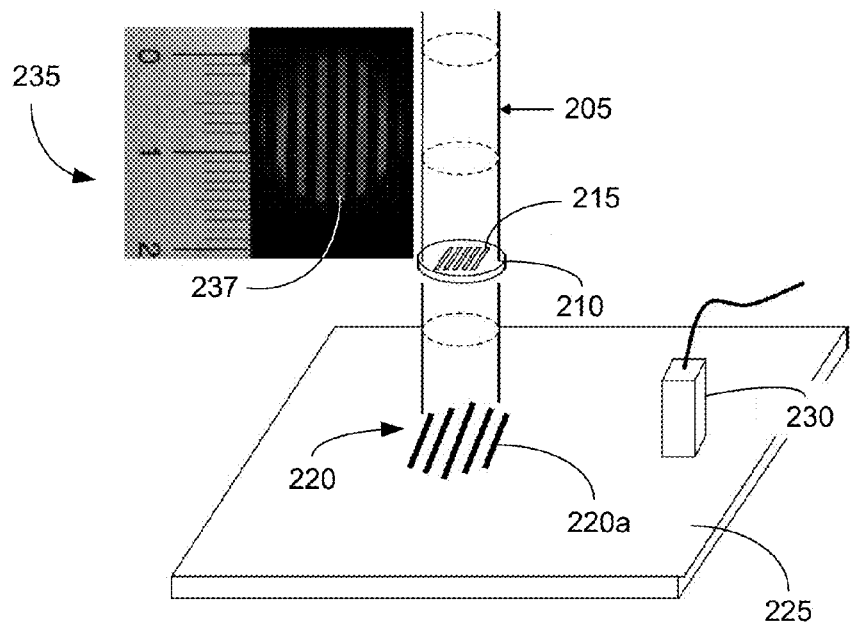
FIG. 3a depicts an experimental setup for a conventional pattern source configuration for inducing ultrasonic waves in a sample.
Figure 3B:
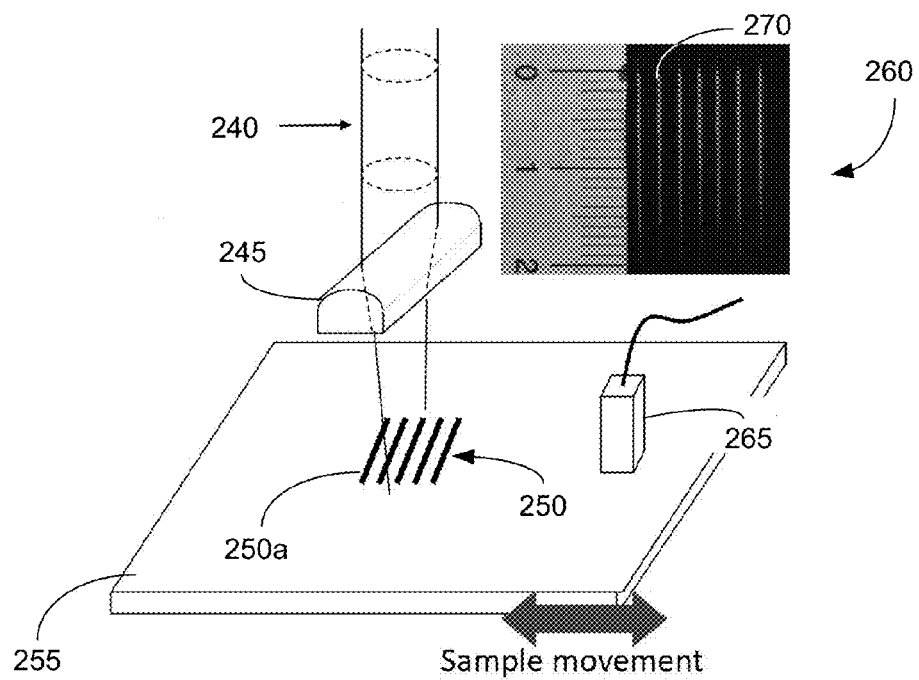
FIG. 3b depicts an experimental setup for a line source configuration for inducing ultrasonic waves in a sample, in accordance with some embodiments of the present invention.

As shown in FIG. 3b, a laser beam can be directed through a cylindrical lens to form a line source that illuminates the surface of the sample and generates ultrasonic waves. In a preferred embodiment, a lens, or a set of lenses, can be used to collimate the laser beam before it is focused. Collimating the beam is not strictly necessary; however, as the laser beam can nonetheless be focused into a line source with the proper tool (e.g., a shadow mask). The laser can be any suitable laser such as, for example, a Continuum Lasers Inlite II-20 pulsed Nd:YAG laser. In other embodiments, other non-contact energy sources such as, for example and not limitation, an EMAT (electromagnetic acoustic transducer) can be used to generate ultrasounds.

The laser can produce a pulsed output at a suitable frequency. In some embodiments, the laser can be operated such that the material stays within the thermoplastic regime to prevent damage to the sample. In other embodiments, such as when a stronger ultrasonic signal is required (e.g., for larger samples) a higher energy beam can be used, though some ablation may occur. To provide NDT for thin plates, for example, a preferred embodiment of the laser can produce a firing repetition rate of approximately 20 Hz and a firing energy of approximately 46 mJ per pulse. In other embodiments, lasers with higher frequencies can be chosen for improved resolution, but these lasers generally increase cost. The energy level can be chosen to stay within the thermoplastic regime, or can be increased to enter the ablation regime. This decision is material and application specific.

The waves induced in the sample by the laser can be received using, for example and not limitation, comb transducers, wedges, waves from liquid media, and electromagnetic acoustic transducers (hereinafter, "EMAT" or "sensor"). In a preferred embodiment, an EMAT with a suitable bandwidth based on the sample size and predicted operating frequencies can be used. To provide NDT for thin plates, for example, a preferred embodiment of the EMAT can have a bandwidth of approximately 500 Hz to 2.5 MHz. Of course, different materials, material thicknesses, and other parameters could dictate the use of an EMAT with a different bandwidth. The data received by the EMAT can be gathered using an appropriate data acquisition system.

Frequency and Traveling Speed Evaluation of Narrowband Lamb Waves

The theory and application of Lamb waves is known in the art. A key characteristic of Lamb waves is their dispersive nature. One consequence of this dispersive nature is that their phase and group velocities vary with frequency. Because laser generated ultrasound is broadband in nature for a given mode, therefore, different frequency components travel at different speeds and thus, interfere and present an obstacle to signal interpretation. This problem can be addressed by generating narrowband Lamb waves with a fixed wavelength, however, that contain a dominant frequency, which can enable the traveling speeds of different modes to be determined from standard dispersion curves.

Figure 2A:
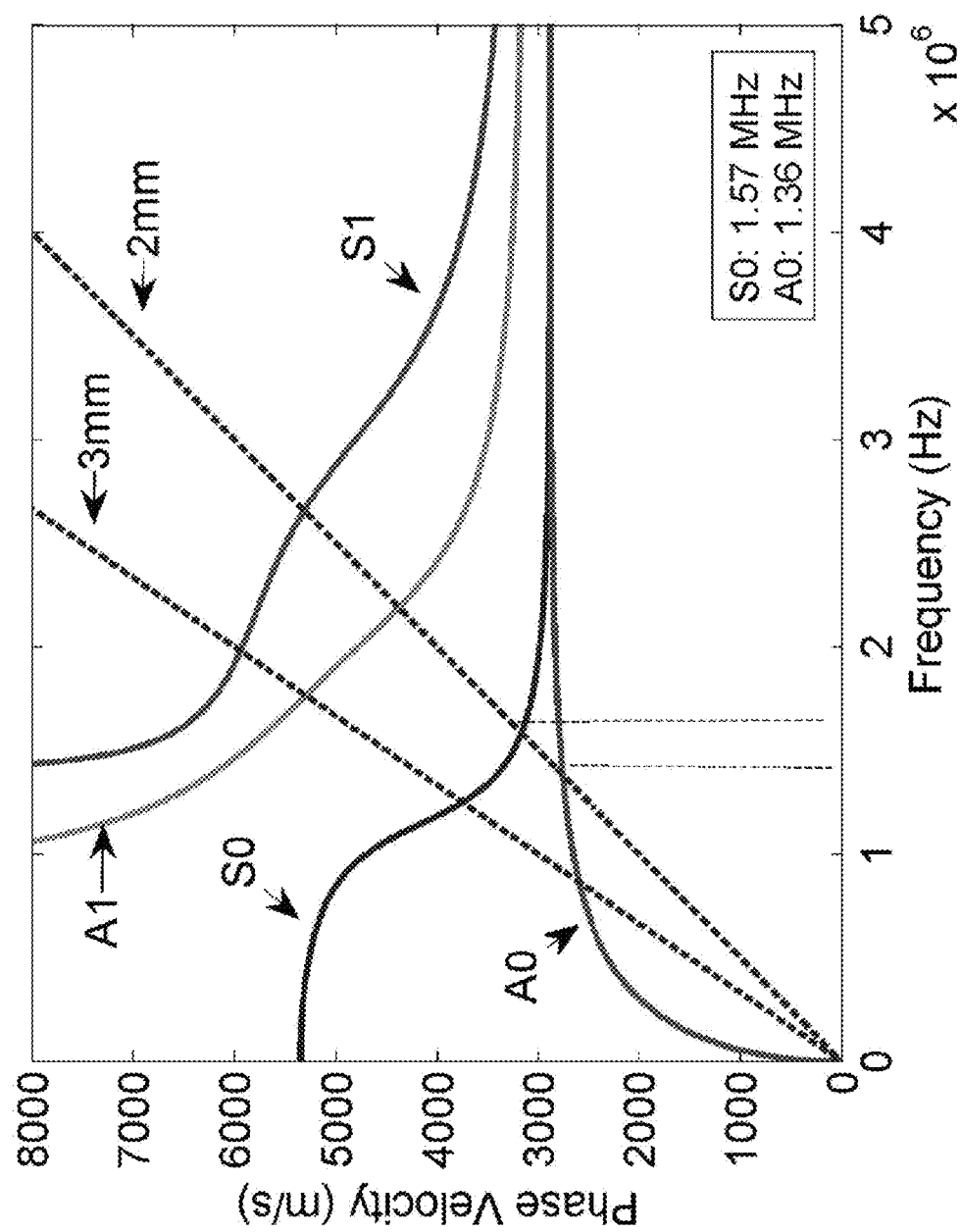
FIG. 2a is a graph depicting the relationship between phase velocity and frequency for multiple modes of antisymmetric and symmetric Lamb wave modes.

FIG. 2a shows the dispersion curves of phase velocity, $C_p$, versus frequency in a 2 mm aluminum plate. In the graph, wavelengths can be represented as straight lines passing through the origin with a slope equal to the wavelengths. If the wavelength of the narrowband Lamb waves can be pre-determined, the frequency content of each mode can be determined by the x-coordinate of the intersection between the line and the dispersion curves.

Figure 2B:
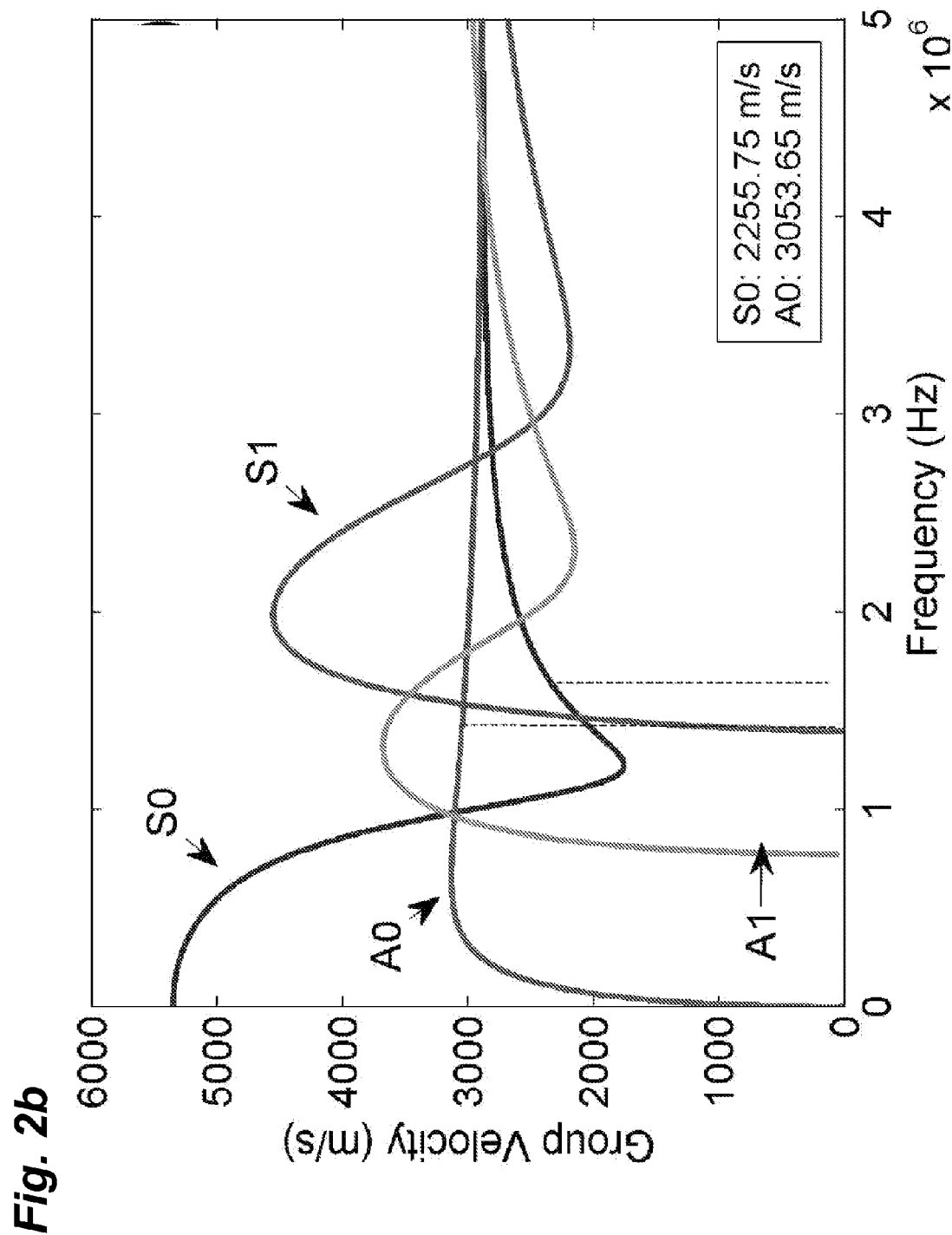
FIG. 2b is a graph depicting the relationship between group velocity and frequency for multiple modes of antisymmetric and symmetric Lamb wave modes.

In FIG. 2a, for example, the x coordinate of the intersection between the straight line of 2 mm wavelength and $S_0$ dispersion curve is at approximately 1.57 MHz and approximately 1.36 MHz for $A_0$ mode. Once the dominant frequency of each mode is determined, the traveling speed can be determined by dispersion curves of group velocity versus frequency as shown in FIG. 2b in which, the traveling speeds ("$C_g$") of $S_0$ and $A_0$ modes are 2255.75 and 3053.65 m/s respectively. Table 1, below, summarizes the frequencies and wave speeds of $S_0$ and $A_0$ modes with different wavelengths and plate thicknesses.

TABLE 1

Frequency Contents and Traveling Speeds of Lamb Modes

| | Plate thickness = 1.5 mm | | | | Plate thickness = 2.0 mm | | | |
|---|---|---|---|---|---|---|---|---|
| | $\lambda$ = 2 mm | | $\lambda$ = 3 mm | | $\lambda$ = 2 mm | | $\lambda$ = 3 mm | |
| Mode | Frequency (MHz) | $C_g$(m/s) | Frequency (MHz) | $C_g$(m/s) | Frequency (MHz) | $C_g$(m/s) | Frequency (MHz) | $C_g$(m/s) |
| S0 | 1.92 | 1861.12 | 1.55 | 2080.02 | 1.57 | 3255.75 | 1.24 | 1777.90 |
| A0 | 1.56 | 3078.50 | 0.97 | 3125.90 | 1.38 | 3053.65 | 0.85 | 3118.65 |

Superimposed Line Sources (SLS)

Conventionally, as shown in FIG. 3a, narrowband laser generated ultrasound has been created using a pattern source. To create a pattern source, the laser beam 205 is first expanded and collimated and the beam 205 goes through a shadow mask 210 with slits 215. The obvious result is that a portion of the laser beam 205 passes through the slits 215 and the remainder is blocked (reflected or absorbed) by the mask 210. The effect of the generated pattern source 220 can be treated as independent line sources 220a illuminating on the surface of the sample 225 simultaneously. Because of constructive interference over the space, narrowband ultrasound with the designated wavelength can created as determined by the spacing of the mask. The resulting narrowband signal can be captured by a sensor 230 (e.g., an EMAT). It should be noted, however, that the portion of the laser energy that is blocked by the mask 210 is wasted resulting in dimmer, less focused pattern sources 237, as illustrated by the laser alignment paper 235.

In contrast, using SLS, as shown in FIG. 3b, the laser beam 240 is focused by a cylindrical lens 245 to create a laser line source pattern 250. Again, the effect of the generated pattern source 250 can be treated as independent line sources 250a illuminating on the surface of the sample 225 simultaneously. In this configuration, substantially all (other than some possible diffraction in the lens) of the laser beam 240 energy is transmitted to the sample 255 and, as shown on the laser alignment paper 260. A brighter, more focused line source 270 is created. The stronger line pattern 250 results in a stronger, more coherent ultrasonic signal in the sample 255. The ultrasonic signal induced by each line source 250a is acquired by the sensor 265 and stored in computer memory individually. As discussed below, narrowband signals of a particular wavelength can then be superimposed using, for example, software to amplify signals of a desired frequency and reduce signal complexity.

EXAMPLE 1

To compare the efficacy of the SLS method versus the conventional pattern source method two preliminary experiments were conducted on a 300×200×2 mm aluminum plate. FIGS. 3a and 3b show the schematic of the experiment and the placement of the sensors and the sources for the conventional pattern source (FIG. 3a) and the SLS (FIG. 3b), respectively. FIG. 3a depicts the experiment using a pattern source 220 where the laser beam 205 goes through a mask 210 with eight slits 215. Each slit 215 is 1 mm wide and 15 mm long and the pitch between slits 215 is 2 mm. Also shown is a laser mark 237 of the pattern source 220 on the laser alignment paper 235. The width of each stripe is about 1 mm and the pitch is 2 mm.

FIG. 3b shows the experiment using SLS where the laser beam 240 goes through a cylindrical lens 245 and the beam 240 is focused into a line source 250. Laser marks with 2 mm pitch are shown on laser alignment paper 260. Compared with the lines 237 in FIG. 3a, the laser energy is clearly more focused and each line 270 is much narrower than the stripe of the pattern source 220. The signal induced by the line source 250 is then acquired by the EMAT 265.

Figure 4A:
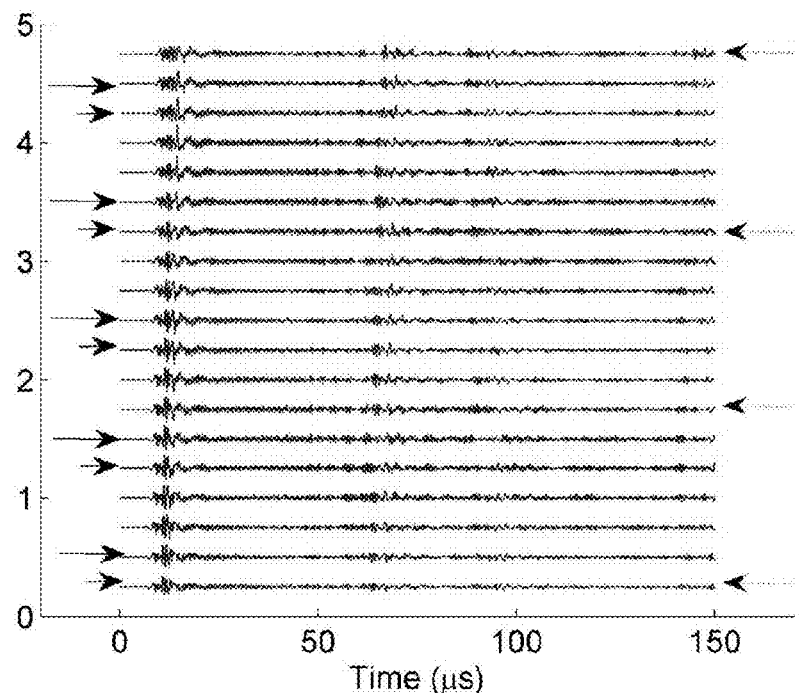
FIG. 4a is a graph depicting a plurality signals generated at multiple intervals along the sample, in accordance with some embodiments of the present invention.

After signal acquisition in the initial position, a motorized linear stage moves the sample 255 and the EMAT 265 in 0.5 mm increments while the laser source 250 is fixed and signals induced by separate line sources 250a are acquired. An example of acquired signals is shown in FIG. 4a where a signal is generated at each 0.5 mm increment. The increment for sampling is preferably chosen to be smaller than the desired wavelength and can be chosen to balance the cost and time necessary to conduct the measurements with the necessary or desired resolution. In other words, more samples may provide more or better information, but this must be balanced against the time and expense of taking same. By superimposing signals generated at the pitch corresponding to the desired wavelength, an artificial pattern source can be created. The superposition of signals pointed to by the dashed arrows to the right of the graph, for example, correspond to a 3 mm artificial pattern source. The short solid arrows on the left side of the graph correspond to a 2 mm source. Similarly, the long solid arrows on the left side of the graph indicate another 2 mm source, but shifted by 0.5 mm (five signals are superimposed together).

Figure 4B:
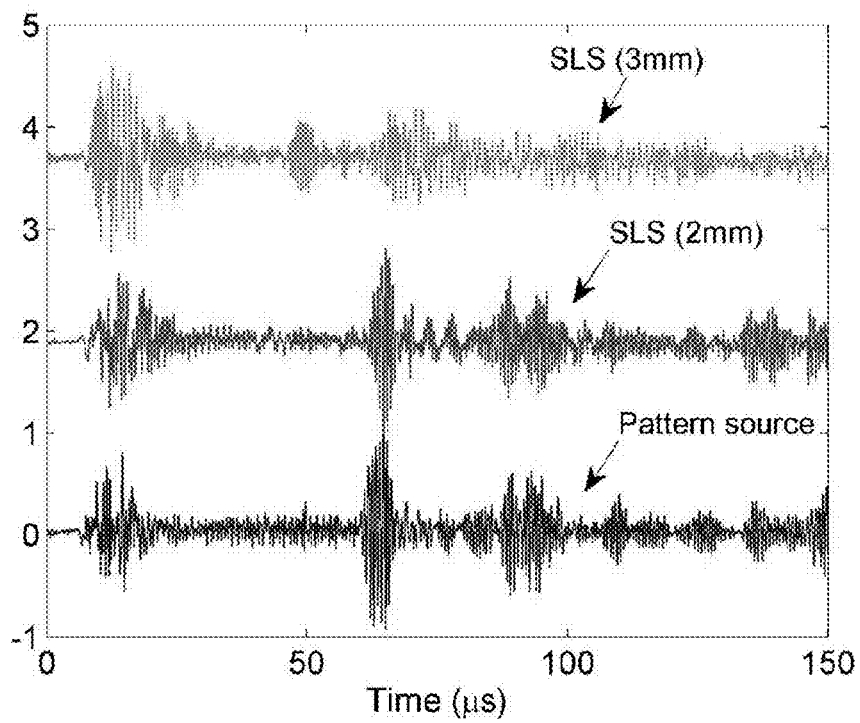
FIG. 4b is a graph comparing signals generated using embodiments of the present invention with signals generated using a conventional pattern source.

The signals corresponding to each pattern source can be superimposed (i.e., summed) to produce amplified signals. FIG. 4b depicts examples of signals from a conventional 2 mm pattern source (bottom), a 2 mm SLS source (middle) and a 3 mm SLS source (top) in the time domain. To enable comparison, for the pattern source, the distance between the source (i.e., the middle of the pattern) and the receiver is approximately 30 mm and, for the SLS, the seven signals that are superimposed are chosen so that the middle signal is also approximately 30 mm away from the receiver. In FIG. 4b, the signals are normalized with their own maxima. As shown in the figure, the signals corresponding to 2 mm produced by the SLS technique are very similar to those produced by the conventional pattern source.

Mathematical Equivalence

The SLS technique can also be shown to be mathematically equivalent to the conventional pattern source technique given some assumptions. Assume, for example, that the response of the wave field for a single line source 220a is h(x,t), and the pattern source 220 is made of perfect line sources 220a and linearity holds. In the following equations, x denotes the distance between the point of interest on the sample 225 and the first line source 220a (it can be positive or negative depending on the signs of the coordinate system) and t denotes time. The response of the wave field of the pattern source 220 can be expressed as a convolution sum in space and the mathematical expression is shown in Eq. 1:

$$f(x,t) = h(x,t) * g(x) \quad (1)$$

where f(x,t) is the response of the pattern source 220 and h(x,t) is the response of a single line source 220a and g(x) is the input sequence for a pattern source 220 which can be expressed as multiple Dirac delta impulses that are separated by the distance corresponding to the wavelength as in Eq. 2.

$$g(x) = \sum_{i=0}^{n} \delta(x - i\lambda) \quad (2)$$

where δ is the distance between line sources 220a and it corresponds to the desired wavelength to be generated, n stands for the total number of line sources 220a that constitute the pattern source 220, and i is the index of the line source 220. When i is zero, it denotes the first line source 220a. Substitute Eq. 2 into Eq. 1 and the response of the pattern source 220 can be derived. The derivation of the convolution is shown in Eq. 4:

$$f(x,t) = \sum_{\xi=-\infty}^{\infty} h(x-\xi, t)g(\xi) \quad (3)$$
$$= \sum_{\xi=-\infty}^{\infty} h(x-\xi, t)\left(\sum_{i=0}^{n} \delta(\xi - i\lambda)\right)$$

Since the first term is independent of i, the summation over i can be moved to the front and the order of two summations can be interchanged. Eq. 3 becomes Eq. 4.

$$\sum_{i=0}^{n}\sum_{\xi=-\infty}^{\infty} h(x-\xi, t)\delta(\xi - i\lambda) = \sum_{i=0}^{n} h(x - i\lambda, t) \quad (4)$$

Eq. 3 and Eq. 4 show that the wave field of a pattern source 220 that consists of n+1 line sources 220a, with a pitch of δ, is actually the superposition of n+1 shifted replicates of the wave field of a single laser line source 220a and the interval between each replicate is the wavelength. It should be noted that the superposition can be performed after all signals have been stored in the computer memory, which enables later wavelength selection and processing.

Signal Processing Procedure

Embodiments of the present invention can further comprise a signal processing method. The signal processing method can include multiple parts including, but not limited to, (1) wavenumber-frequency (k-ω) domain filtering and (2) continuous wavelet transforms. An objective of this method is to reduce the complexity of signals and to identify originations of wave packets so as to facilitate the calculation of reflection coefficients resulting from the presence of one or more defects.

Figure 5:
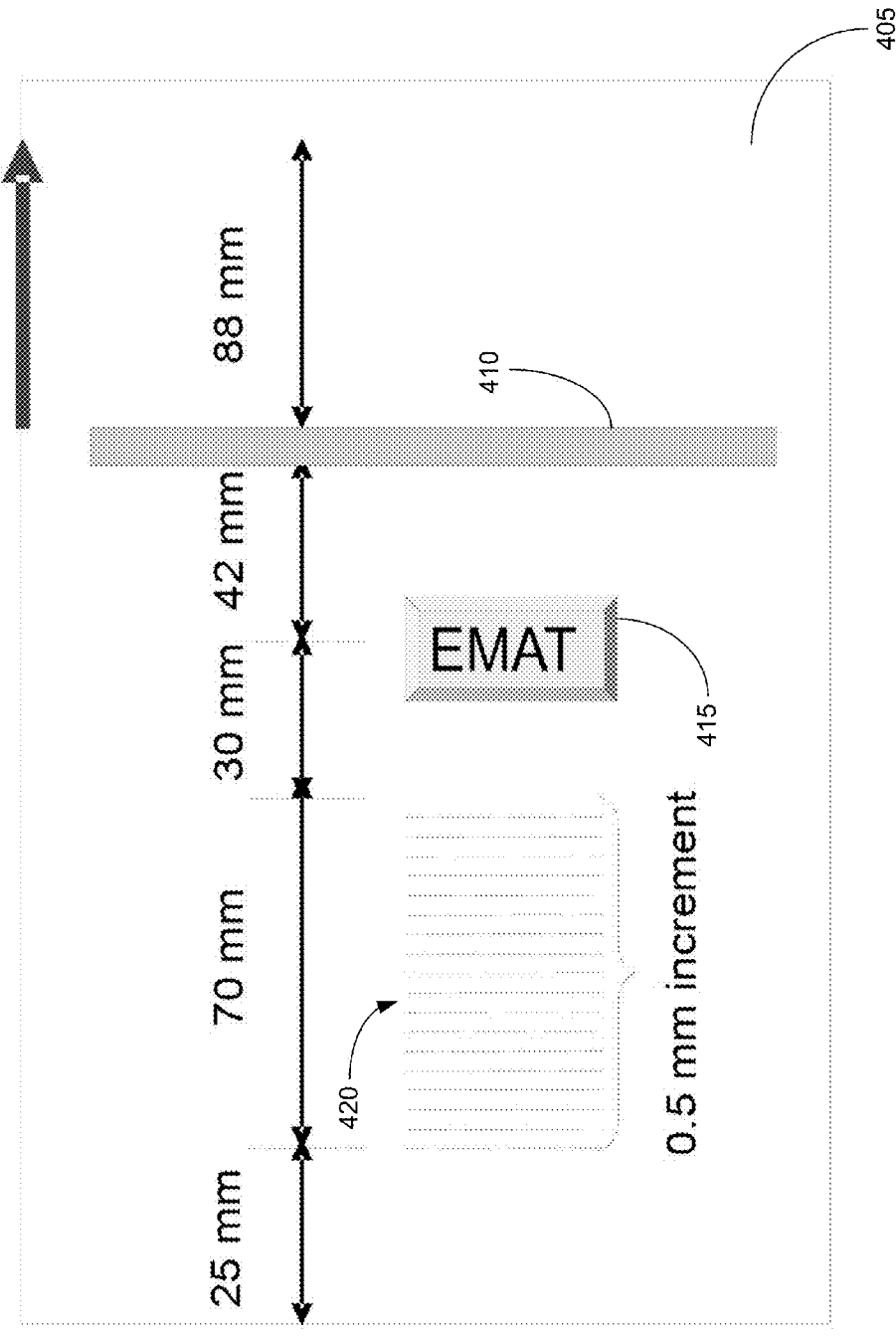
FIG. 5 depicts another experimental setup for a line source configuration for inducing ultrasonic waves in a sample with a defect, in accordance with some embodiments of the present invention.

To illustrate the signal processing procedure, an experiment as depicted in FIG. 5 can be conducted on a 2 mm aluminum plate 405. The plate 405 is held on a motor driven linear stage and a laser line source 420 is used to generate ultrasounds. On the sample 405, there is an artificial groove 410 which is 0.8 mm wide and 1.75 mm deep. When conducting the experiments, the laser beam is fixed and the sample 405 and the EMAT 415 are moved by the linear stage at 0.5 mm increments. At each location, 32 signals are acquired and averaged to increase signal-to-noise ratio. After all ultrasonic signals have been stored into computer memory, the superimposed laser sources are generated by superimposing every five signals corresponding to 2 mm wavelength together.

Figures 6A, 6B, 6C, 6D:
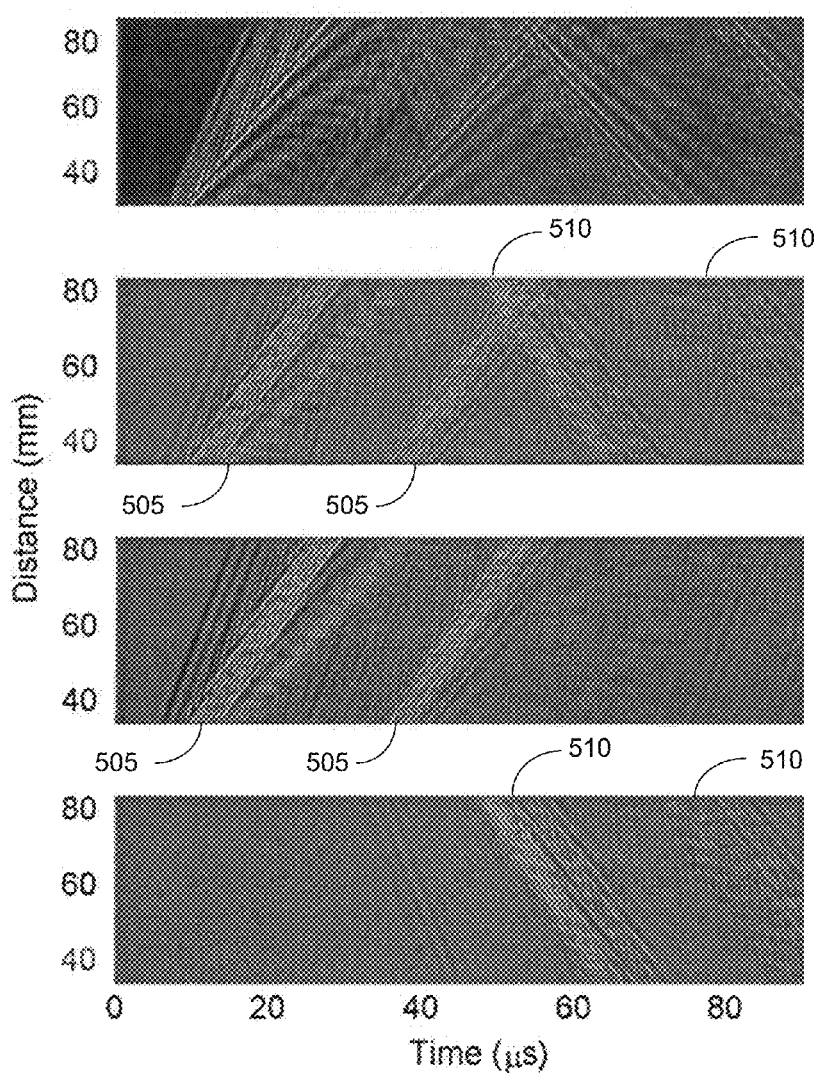
FIGS. 6a-6d depict wave forms of decreasing complexity as they are processed using embodiments of the present invention.

FIG. 6a shows the scan of the original signals, where the X axis denotes time and the Y axis denotes the distance between laser line sources 420 and the EMAT 425. As shown, without superimposition of the signals, considerable complexity exists making the graph difficult to interpret. FIG. 6b, on the other hand, shows the results of the SLS technique. The gray scale of the plots represents relative signal amplitude; although, the contrast and brightness are adjusted for the clarity of the plots. There are some wave fronts featuring positive slopes 505 and some featuring negative slopes 510 indicating waves with increasing or decreasing distance of travel, respectively, as the laser source 420 is moved away from the defect 410 and the EMAT 415.

The signals can be further simplified using additional techniques. The two-dimensional Fourier transform (2D FT) method, for example, is known in the art. It is widely used, for example, to measure the dispersion curves of Lamb waves and can be used to identify and measure the amplitudes of individual Lamb modes. It is also a critical step in wavenumber-frequency domain filtering technique. When full wavefield measurements are transformed into wavenumber and frequency domain by 2D FT, waves traveling in different directions will have different signs in wavenumber. By separating components with different signs in wavenumbers, waves traveling in the different directions can be separated. In this case, waves traveling with increasing 505 or decreasing 510 distance of travel can be separated.

Figure 7:
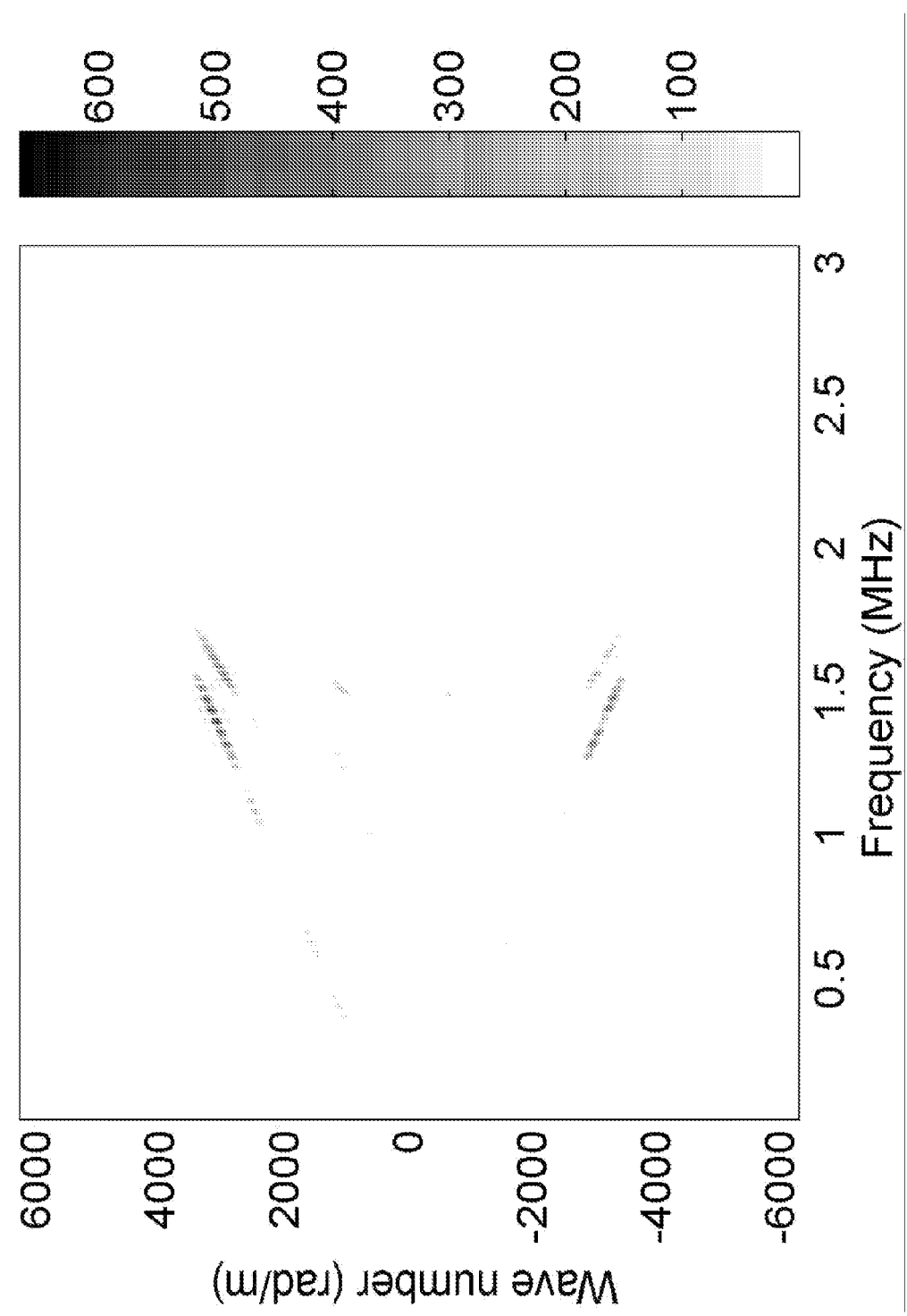
FIG. 7 depicts wave forms that have been simplified using a two-dimensional Fourier transform, in accordance with some embodiments of the present invention.

To illustrate this, the result of 2D FT of FIG. 6b is shown in FIG. 7 in which the X axis denotes frequency, the Y axis denotes wavenumber, and the brightness represents signal amplitude (the gray scale is reversed for the clarity of the graph). FIG. 7 shows the signals of FIG. 6b in k-ω domain in which four bright stripes can be seen. The image is basically symmetrical about the x axis. The image comprises four stripes, with two stripes centered on approximately 1.36 MHz at ±3141 rad/m and the other two centered on approximately 1.57 MHz at ±3141 rad/m. Not coincidentally, wavenumber 3141 rad/m corresponds to a wavelength of 2 mm. To apply k-ω domain filtering, the components with positive wavenumbers and negative wavenumbers can be filtered out separately and then returned to the space-time representation by taking the inverse 2D FT of the filtered signals.

The results are shown in FIG. 6c (positive slope) and 6d (negative slope). Compared with FIG. 6b, it is clear that the wave fronts with positive slopes 505 and negative slopes 510 have been separated successfully and the complexity of signals is greatly reduced. In addition, because the direct incident waves and reflection waves from the defect 410 have increasing distance of travel as the source 420 is moved away from the EMAT 415, FIG. 6c contains all the information necessary to calculate the reflection coefficients.

Laser generated ultrasonic signals are intrinsically non-stationary, non-periodic and broadband. Although Fourier transform is widely used to obtain frequency information in signals, it is not suitable for non-stationary signals due to the fact that it cannot retain time information. Unlike Fourier transform, however, different wavelet functions can be used in wavelet transforms depending on the application and signals of interest. This characteristic makes wavelet transforms flexible and powerful. Wavelet analysis can approximate a signal with shifted and scaled versions of a mother wavelet. Signals with sharp changes, for example, can be better analyzed with an irregular wavelet than with a smooth periodical sinusoid as used in Fourier analysis.

FIG. 8a shows the one time-domain signal of FIG. 5b when distance between source 420 and the EMAT 415 is 70 mm. From the time-domain signal, it can be difficult to identify the wave packets of different wave modes. Although some wave packets can be distinguished, others can overlap and interfere with each other in time. FIG. 8b, on the other hand, shows the time-frequency representation of the same signal in the frequency range 1 MHz to 2 MHz. The transformation is done using the complex Morlet mother wavelet. The complex Morlet mother wavelet can be defined as:

$$\Psi(t) = \frac{1}{\sqrt{\pi f_b}} \exp(2i\pi f_c t) \exp\left(-\frac{t^2}{f_b}\right) \quad (5)$$

where $f_b$ is a bandwidth parameter and $f_c$ is the wavelet center frequency. $f_b$ and $f_c$ are application and signal dependent which, in this case, can be chosen to be, for example, 10 and 1.5 MHz respectively. $f_c$ is preferably chosen to be close to the frequency content of the signal that is of interest, e.g., the center frequency of the received signal $f_b$ can be used to control the tradeoff between frequency and time resolution in the CWT.

By generating narrowband ultrasound signals, the frequency contents and propagating group velocities of different modes can be evaluated. And based on the geometry and the placement of the source 420, sensor 415, defect 410, and the dimension of the tested sample 405, the time of flight (TOF) of each wave can be calculated. By transforming the time domain signal into time-frequency representation, the wave packets can be more easily identified based on the TOF and frequency information. In FIG. 8b, for example, it is clear that there are two main frequency components in the signal. One is centered on approximately 1.36 MHz and the other is centered on approximately 1.57 MHz. Referring back to Table 1, these frequencies can be readily identified as the $A_0$ and $S_0$ modes respectively.

In addition, based on the TOF information, the originations of, for example, directed incident and reflected wave packets from the defect 410 can also be identified. In this example, the distance between the source 420 and EMAT 415 is 70 mm. According to Table 1, the group velocities of $A_0$ and $S_0$ are 3053.65 m/s and 2255.75 m/s, respectively. The TOF for direct incident waves of these two modes are 22.92 µs (i.e., 70 mm/3053.65 m/s) and 31.03 µs, respectively. Similarly, the distance of travel for a reflected wave packet from the defect is 154 mm so the TOF for reflected $A_0$ and $S_0$ from the defect are 50.43 µs and 68.27 µs respectively. As a result, the incident $A_0$, $S_0$ and reflected $A_0$, $S_0$ waves can be identified as labeled in FIG. 8b and the reflection coefficients can be calculated by the division of amplitudes of corresponding wave packets.

EXAMPLE 2

A set of finite element simulation on thin plates can be conducted to show that: (1) SLS has practical applications, and (2) the technique of k-ω filtering coupled with continuous wavelet transform can be used to correlate reflection coefficients to defect severity. To simplify problem at hand, the laser line sources are assumed to be infinitely long in the direction orthogonal to the plane defined by wave propagation and thickness. In this way, the problem can be reduced to a 2D plane strain problem. The material used in the simulation is aluminum with the material properties, i.e., longitudinal ($C_L$) and shear ($C_T$) wave speeds, listed in Table 2, below.

TABLE 2

| Material Properties and Wave Speeds | | | | | |
|---|---|---|---|---|---|
| | E (GPa) | ν | λ (GPa) | μ (GPa) | $C_L$ (m/s) | $C_T$ (m/s) |
| Aluminum | 70 | 0.33 | 51.1 | 26.3 | 6194.4 | 3120.2 |

In some embodiments, the simulation of laser generated ultrasound can be approached as a sequentially solved transient thermo-mechanical problem. The temperature field induced by the laser input can first be solved and the temperature distribution can be taken as a thermal nodal load in the transient structural analysis in each time step. Then the transient displacement field can be solved sequentially. To perform this analysis, two different physical fields of analyses, which share the same geometry and the same mesh but with different element types, can be used. In a preferred embodiment, the element type used in thermal analysis is compatible with the element type used in structural analysis. Commercial software such as, for example and not limitation, Abaqus 6.8 can be used to perform this analysis.

Due to the large temperature gradient over a short period of time at the location where the laser illuminates the sample, fine mesh is preferred to capture an accurate transient temperature field. The element size needed for calculating accurate transient structural field (i.e., the area away from the laser in which the waves propagate), on the other hand is less demanding enabling the use of a coarser mesh. In a preferred embodiment, a smooth transition from the fine mesh to the coarse mesh is provided with a mesh size smaller than approximately one-sixth of the wavelength. In this example, therefore, a mesh size of 100 μm is used in the wave propagation region and a mesh size of 5 μm is used in the laser input region.

In some embodiments, two time steps can be used in the analysis, the laser-on stage and the laser-off stage. During the heat input (i.e., laser irradiating) stage, the time step is set to a small interval (e.g., 1 ns in this example) to capture the rapid change of temperature distribution from the laser. Afterwards, the time step can be set to a larger interval (e.g., 25 ns) for the remainder of the analysis. In some embodiments, the appropriate time step can be chosen to correspond to the time the fastest possible wave propagates between successive elements in the mesh. In this configuration, the fastest wave is a longitudinal wave with a speed of approximately 6000 m/s, thus the choice of 25 ns is appropriate.

The thermal loading condition in the simulation can be described as follows:

$$-k \frac{\partial T(x, y, t)}{\partial y}\bigg|_{top\_surface} = I_0 A(T) f(x) g(t) \quad (6)$$

where k is the thermal conductivity, $I_0$ is the incident laser energy density, the total energy is set to be 46 mJ (i.e., the setting used in this example), and A(T) is the optical absorptivity of the specimen surface. For aluminum, the optical absorptivity is as follows, where T is in Celsius.

$$A(T) = 5.2 \times 10^{-2} + 3 \times 10^{-5}(T-27) \quad (7)$$

f(x) and g(t) are the spatial and temporal distributions of the laser pulse, respectively. These two functions can be written as:

$$f(x) = \exp\left(-\frac{x^2}{x_0^2}\right) \quad (8)$$

$$g(t) = \frac{t}{t_0} \exp\left(-\frac{t}{t_0}\right) \quad (9)$$

where $x_0$ and $t_0$ are set to be 300 μm and 10 ns, respectively, in this example.

Figure 9:
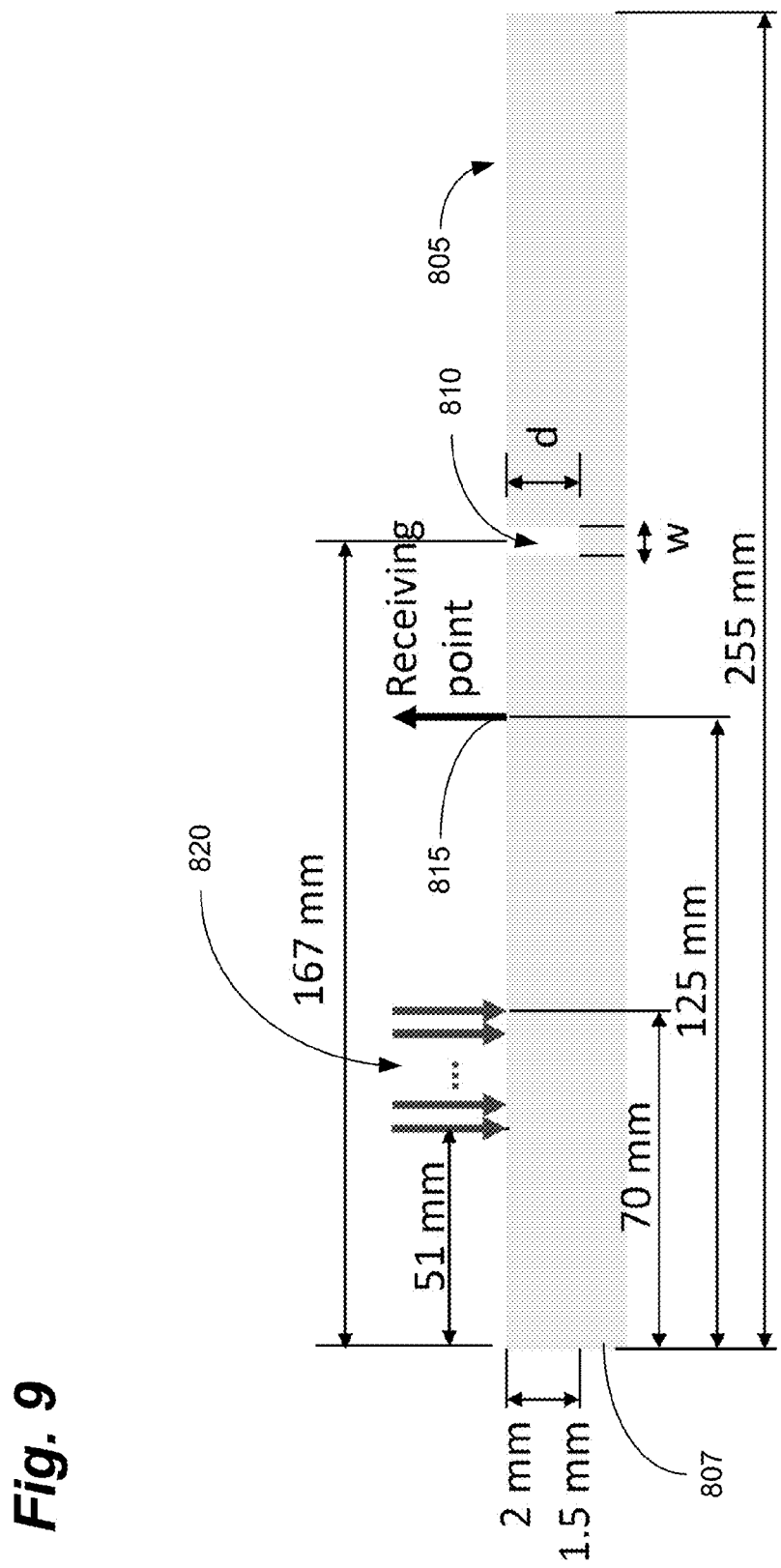
FIG. 9 depicts yet another experimental setup for a line source configuration for inducing ultrasonic waves in a sample with a defect, in accordance with some embodiments of the present invention.

The experimental setup for this example is shown in FIG. 9. The length of the plate 805 is 255 mm and the thickness is either 1.5 mm or 2 mm. A surface breaking notch 810 is located 170 mm away from the left end 807 of the plate 805. The width, w, of the notch 810 is 0.8 mm and the depth, d, is increased from ⅛ of the plate thickness to ⅞ of the plate thickness in increments of ⅛ of the thickness of the plate.

The receiving point 815 is located 125 mm away from the left side 807 of the plate 805. For a given notch depth, ultrasonic signals are generated separately by 20 single line sources 820 located between 51 mm and 70 mm away from the left end 807 of the plate 805 in 0.5 mm intervals. As before, wavenumber-frequency domain filtering can be performed on these signals to separate ultrasounds propagating in different directions. After the ultrasonic signals are simplified, narrowband signals corresponding to 2 mm and 3 mm wavelengths can be created by superimposing every five signals together.

The narrowband signals can then be processed by the above mentioned techniques to identify the wave packets induced by different sources. The reflection coefficients due to the notches can be calculated by dividing the amplitudes of the reflected waves by those of incident waves. The simulation results are shown in FIGS. 10a-10d.

EXAMPLE 3

To validate the simulation results, a set of experiments can be conducted. The experimental setup can be the same as the setup depicted in FIG. 5 and the testing procedure can be substantially the same as the procedure previously described. See, "Signal Processing Procedure" section, above. On each sample, an artificial groove is made to simulate a surface breaking defect. In the example, the plate thickness is 2 mm and the grooves are 0.8 mm wide and vary in depth. Seven depths are used in these experiments: 0.25, 0.50, 0.75, 1.00, 1.25, 1.50, and 1.75 mm (i.e., ⅛, ²⁄₈, ⅜, ⁴⁄₈, ⅝, ⁶⁄₈ and ⅞ of the plate thickness). A set of five signals that correspond to 2 mm or 3 mm wavelength are superimposed and then processed using the signal processing procedure discussed earlier. Reflection coefficients can then be calculated and compared with simulation results. The results and comparison are shown in FIGS. 11a-11d.

Discussion of Simulation and Experimental Results

In FIGS. 10a-10d, the simulation results of the reflection coefficients of modes $A_0$ and $S_0$ with different plate thicknesses and wavelengths are presented. In the figures, the legend "$A_0 \rightarrow A_0$" denotes the coefficients corresponding to incident $A_0$ mode and reflected $A_0$ mode and the legend "$S_0 \rightarrow S_0$" denotes the coefficients corresponding to incident $S_0$ mode and reflected $S_0$ mode. As expected, the strength of the reflection coefficients increases with the severity of the defects, however, most of them do not increase monotonically.

Figure 10B:
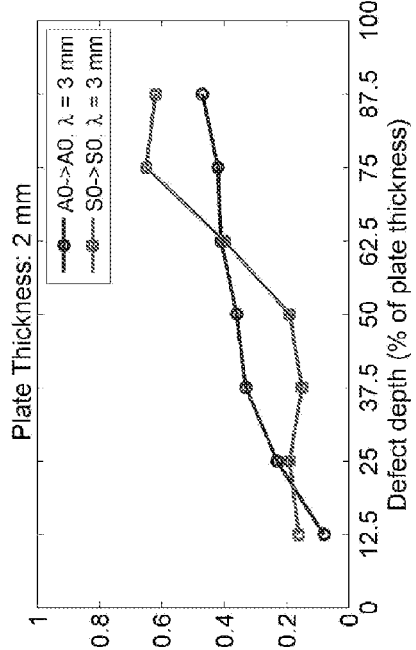
FIGS. 10a-10d depict simulated results for the incident and reflected symmetric and antisymmetric modes, in accordance with some embodiments of the present invention.
Figure 10D:
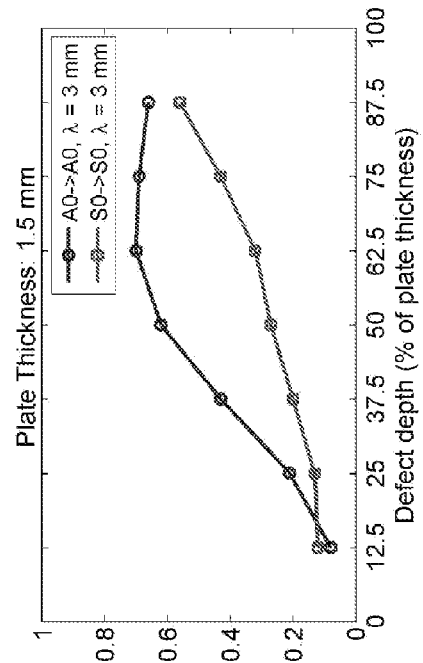
Figure 10A:
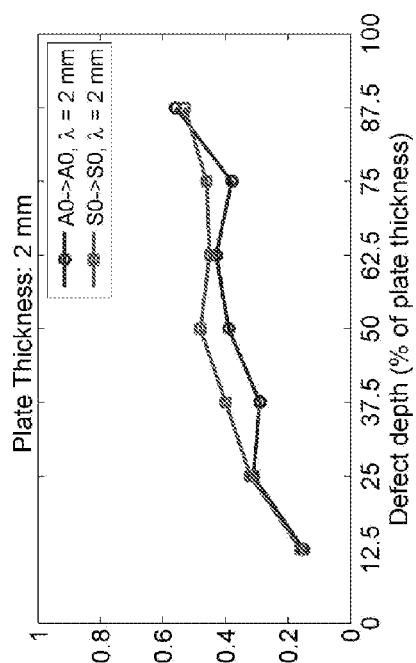

In FIG. 10a, for example, with a plate thickness of 2 mm, the reflection coefficients for $A_0$ mode and $S_0$ mode with a 2 mm wavelength are very similar and the frequency-thickness (f-d) product of $A_0$ mode and $S_0$ mode (using data from Table 1) are 2720 (i.e., 1.36 MHz×2 mm) and 3120 (i.e., 1.57 MHz×2 mm) Hz-m, respectively. Most parts of the reflection coefficients for both cases are between 0.2 and 0.6. In contrast, in FIG. 10b, the reflection coefficient curves of $A_0$ mode and $S_0$ mode with 3 mm wavelength are very different. The f-d product of $A_0$ mode and $S_0$ mode, for example, are 1700 and 2480 Hz-m, respectively. For $A_0$ mode, the coefficients gradually rise with the defect depth. The substantially linear response between the 3 mm $A_0$ mode in a 2 mm plate makes it suitable for use as a calibration curve for quantifying defect depth. For $S_0$ mode, the coefficients are basically constant around 0.2 when the defect depth is below 50% of the plate thickness. This is an unexpected result because the symmetric modes would generally be expected to be more sensitive to asymmetric defects in a plate. One possible explanation is that the energy is reflected in the form of mode conversion, which cannot be measured using the SLS technique.

Figure 10C:
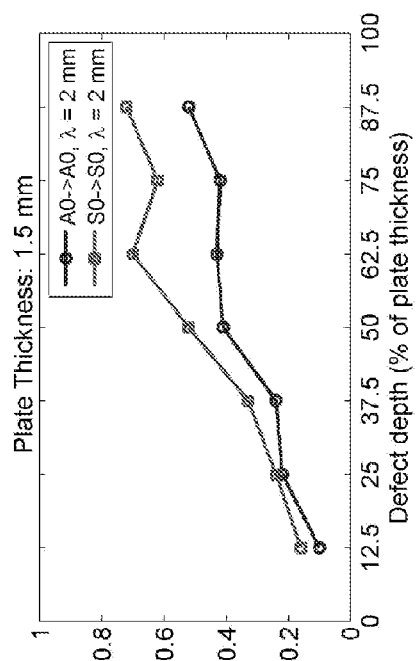
Figure 11B:
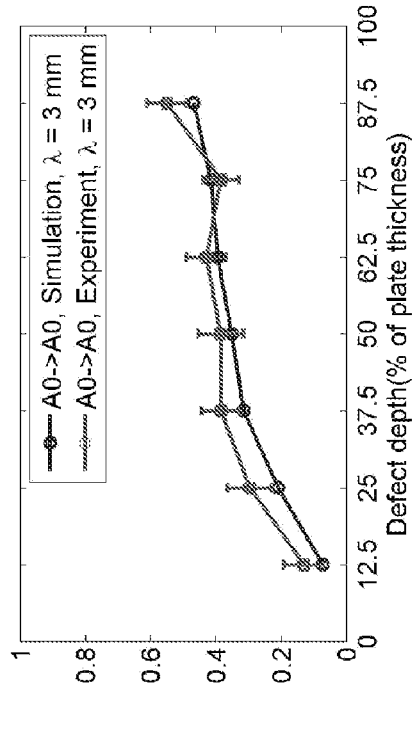
FIGS. 11a-11d compare simulated results with experimental results produced using embodiments of the present invention.
Figure 11D:
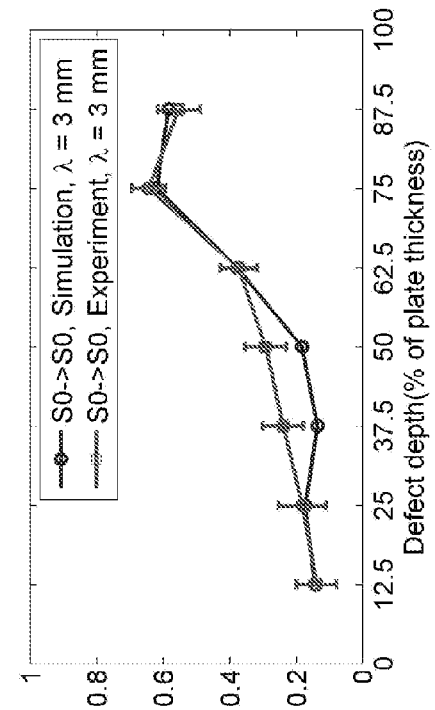
Figure 11A:
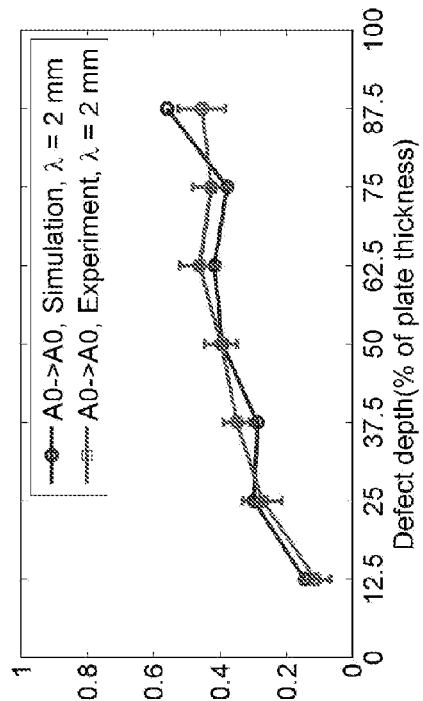
Figure 11C:
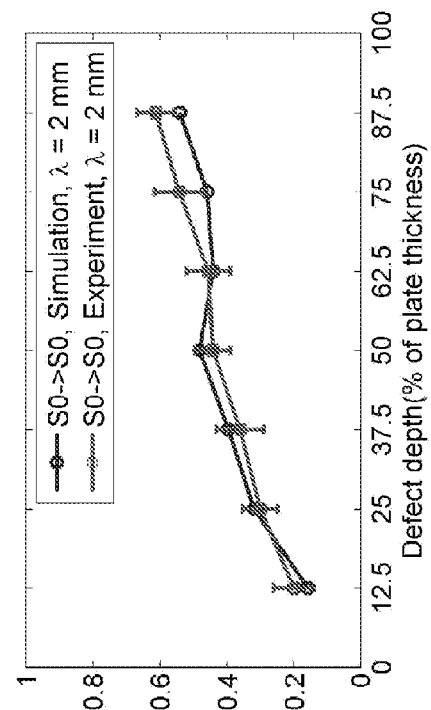

FIGS. 10c and 10d show reflection coefficients when the plate thickness is 1.5 mm. The f-d product of a 2 mm wavelength $A_0$ mode and $S_0$ mode are 2325 and 2880 Hz-m, respectively. The f-d product of 3 mm wavelength $A_0$ mode and $S_0$ mode are 1455 and 2325 Hz-m respectively. The profile of reflection coefficients for $A_0$ mode with 2 mm wavelength shows substantial similarity with the above results from a plate thickness of 2 mm. For 3 mm wavelength, on the other hand, the reflection coefficient of $S_0$ mode increases steadily with defect depth, but the $A_0$ mode levels off when the defect depth is greater than approximately 50% of the plate.

FIGS. 11a-11d shows the comparison between the simulation and experimental results with a 2 mm plate thickness. As shown, there is good correlation between the experimental results and the simulation. Based on the simulation and experimental results, the sensitivities of reflection coefficients to defect depth are quite different in different situations. When the plate thickness is 2 mm and the wavelength is 3 mm, for example, the reflection coefficient of $S_0$ appears substantially insensitive to the shallow defects (i.e., when the depth is less than 1 mm). Under the same conditions, the reflection coefficient of $A_0$, on the other hand, appears substantially insensitive to the defect depths in the middle range (i.e., between 37.5% and 75% of the plate thickness).

Weld Analysis

Embodiments of the present invention can also be used to analyze various characteristics of welds. Weld dimensions are affected by many welding parameters including, but not limited to, electrode extension, arc voltage, welding speed, wire feed rate, etc. It is these weld parameters that determine the quality and ultimately the strength of the weld. As mentioned above, conventionally weld inspection has been done using the cutcheck method. This involves taking samples and literally cutting them across the weld. The characteristics of the weld can then be directly observed and measured.

The cutcheck method is a simple and effective means for analyzing weld quality. It is, nonetheless, wasteful and time consuming. The cutcheck method requires destruction of the sample. The cutcheck method is also not suitable for automated quality control processes as is generally requires manipulation and analysis beyond what can be practically achieved autonomously. The cutcheck method is also not suitable for real-time testing, as they sample must be removed from manufacturing (e.g., the assembly line), cut, and analyzed. Embodiments of the present invention, however, can be used to provide NDT that yields accurate information regarding weld quality using similar techniques to those described above for material defects.

EXAMPLE 4

In a controlled experiment, a range of weld dimensions can be realized by applying different welding parameters. A sample can be made, for example, by welding two pieces of A36 steel plates together with a MIG (or wire feed) welder. The plate measures 254 mm×140 mm×2.5 mm and the weld seam is 216 mm long. The material properties for A36 Steel are listed below in Table 3.

TABLE 3

Material Properties of A36 Steel

| | E (GPa) | ν | λ (GPa) | μ (GPa) | $C_L$ (m/s) | $C_T$ (m/s) |
|---|---|---|---|---|---|---|
| A36 Steel | 200 | 0.26 | 86.0 | 79.4.3 | 5584.3 | 3180.4 |

During welding, the MIG torch is fixed and the samples are moved by a linear stage with a programmable speed. The first set of samples is made by varying four welding parameters to make wide ranges of weld dimensions. These four parameters are contact tip-to-workpiece distance (CTWD), welding speed, arc voltage and wire feed rate (WFR). A four-factor two-level full factorial design of experiment is conducted. The parameters and their levels are shown in Table 4.

TABLE 4

Welding Parameters for Sample Sets

| | First Set Levels | | Second Set Levels | | |
|---|---|---|---|---|---|
| Factor | − | + | − | 0 | + |
| A. CTWD (inch) | 0.5 | 0.8 | | 0.5 | |
| B. Welding speed (in/min) | 17 | 25 | 15 | 20 | 25 |
| C. Arc voltage (Volt) | 18 | 22 | | 18 | |
| D. Wire feed rate (in/min) | 150 | 200 | 150 | 175 | 200 |

There are 16 runs and the run order is randomized to minimize lurking variables that are not identified and the design matrices are shown in Table 5. The second set of samples, also shown in Table 4, is prepared by varying two welding parameters, which are welding speed and WFR. A two-factor three-level full factorial design is implemented for a total of nine runs. To reduce the variability of the weld, the CTWD and Arc voltage are held constant for the second set. The levels chosen for the second set were based on the cutcheck results of the first set.

TABLE 5

Design Matrices for Sample Sets

| | First Set | | | | Second Set | |
|---|---|---|---|---|---|---|
| Run | CTWD | Welding speed | Arc voltage | WFR | Welding speed | WFR |
| 1 | − | − | − | + | − | − |
| 2 | − | − | − | − | − | 0 |
| 3 | − | − | + | + | − | + |
| 4 | − | − | + | − | 0 | − |
| 5 | − | + | − | + | 0 | 0 |
| 6 | − | + | − | − | 0 | + |
| 7 | − | + | + | + | + | − |
| 8 | − | + | + | − | + | 0 |
| 9 | + | − | − | + | + | + |
| 10 | + | − | − | − | | |
| 11 | + | − | + | + | | |
| 12 | + | − | + | − | | |

TABLE 5-continued

Design Matrices for Sample Sets

| | | First Set | | | Second Set | |
|---|---|---|---|---|---|---|
| Run | CTWD | Welding speed | Arc voltage | WFR | Welding speed | WFR |
| 13 | + | + | − | + | | |
| 14 | + | + | − | − | | |
| 15 | + | + | + | + | | |
| 16 | + | + | + | − | | |

Figure 12A:
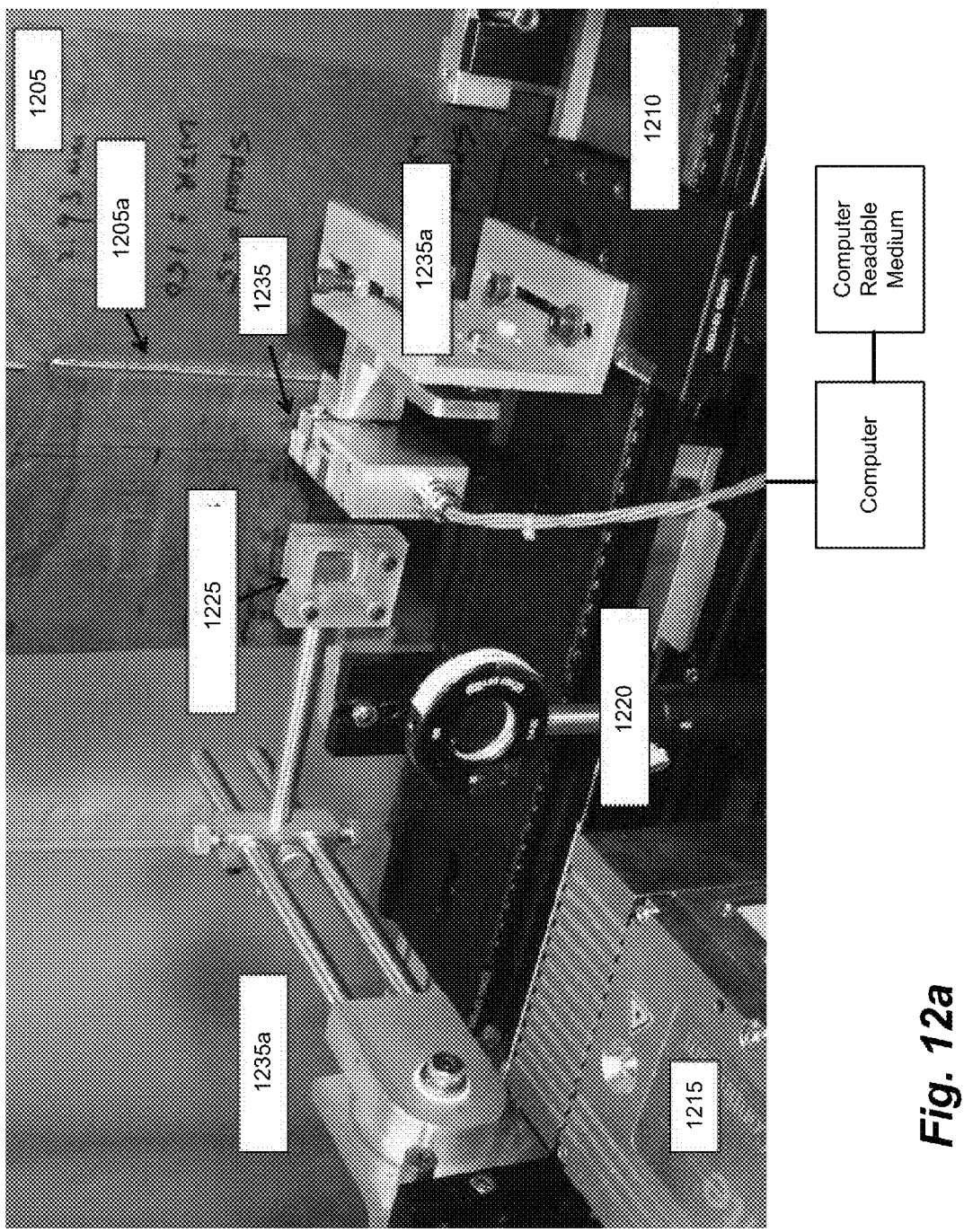
FIGS. 12a and 12b depict yet another experimental setup for a line source configuration for inducing ultrasonic waves in a sample with a butt weld, in accordance with some embodiments of the present invention.
Figure 12B:
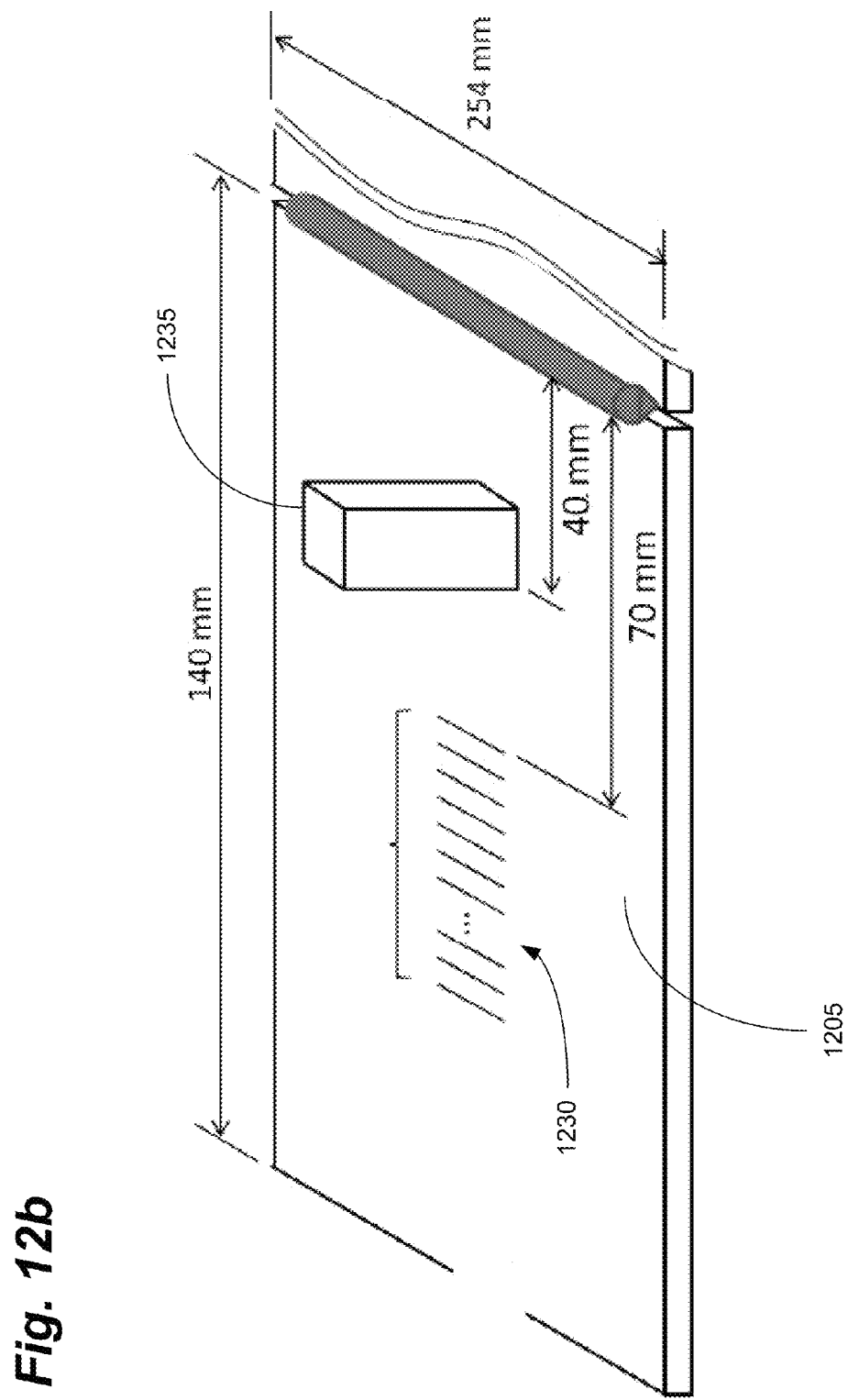

The photo and schematic of the experimental setup are shown in FIGS. 12a and 12b, respectively. A sample 1205 is held vertically on a linear stage 1210. A laser beam 1215 is directed through a concave lens 1220 and then focused by a cylindrical lens 1225 fixed in a mount 1225a to form a line source 1230 which illuminates the surface of the samples to generate ultrasounds. As before, the laser is a Continuum Lasers Inlite II-20 pulsed Nd:YAG Q-switched laser. The repetition rate of the laser is 20 Hz, but the energy per pulse is increased to 56 mJ. An EMAT 1235 with a 0.5-2.5 MHz bandwidth is fixed in a mount 1235a and is used to receive the ultrasonic signals. The laser 1215 and the EMAT 1235 are arranged in a reflection mode so that the EMAT 1235 can capture both the direct incident wave and the reflected waves from the weld seam 1205a.

For the first set of samples, sixteen samples are made, and for each sample, five locations along the weld seam 1205a are inspected. For the second set of samples, nine samples are made, and for each sample, nine locations along the weld seam 1205a are inspected. Similar to the method used for defect detection described above, during the inspection of a particular location, the laser beam 1215 is fixed while the samples and the EMAT 1235 are moved by the linear stage (in this case at 0.25 mm increments). As discussed above, the as long as the increment is smaller than the desired wavelength, its actual size is somewhat arbitrary. In other words, the smaller the increment the higher the resolution, but at a correspondingly higher time and/or monetary cost. At each laser incident location, 32 signals are acquired and averaged to increase signal-to-noise ratio. A total number of 240 averaged signals are stored in a computer linked to the EMAT 1235.

After all of the samples 1205 are inspected nondestructively, cutchecks are performed to measure the dimensions of the welds 1205a. Cross sections of the inspected locations are cut out and mounted onto acrylic pucks which are then ground and polished. The cross sections of the samples 1205 are polished up to grit 800 level and then etched to highlight the boundaries between the weld beads and the base material. The etching solution is nital, or the mixture of 5% nitric acid and 100% methanol by volume. After etching, each puck is scanned by an optical scanner with 1200 dpi (dot-per-inch) resolution and important dimensions are measured.

Figures 13A, 13B, 13C, 13D, 13E, 13F:
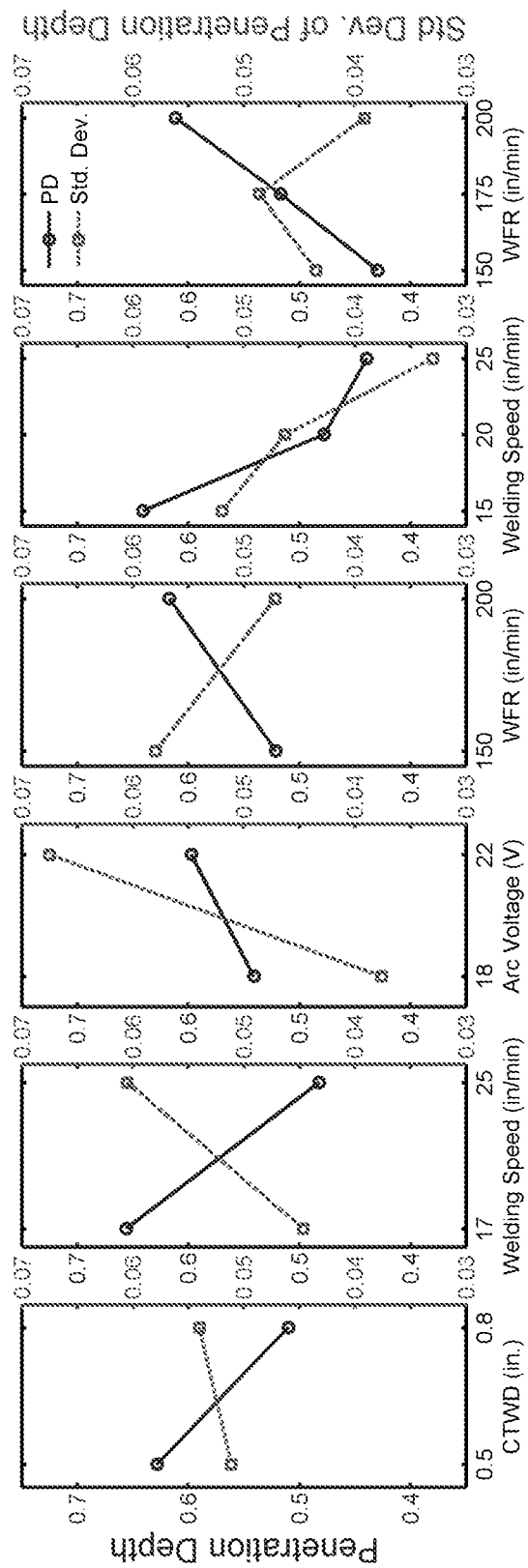
FIGS. 13a-13f depict the relationship between various weld parameters and weld penetration depth.

For the first set of the samples, there are 160 cutcheck locations (10 locations on each of the 16 samples); for the second set of the samples, there are 81 cutcheck locations (9 locations on each of the 9 samples). The main effects plots for penetration depth ("PD") and standard deviation are shown in FIG. 13 in which the solid line plots represent PD and the dashed plots represent their standard deviations. The values of weld dimensions are normalized by the plate thickness.

The second set of samples is prepared by holding CTWD and arc voltage constant and WFR and welding speed are varied because they are easier to control. The CTWD and arc voltage are chosen to be 0.5 inch and 18 V to reduce the variability of the weld. The main effects plots of PD of the second set of samples are shown in FIG. 13 as well. The summary of effects of welding parameters on weld dimensions and variation is listed in Table 6, below.

TABLE 6

Effects of Welding Parameters

| | First set | | | | Second set | |
|---|---|---|---|---|---|---|
| | CTWD | Welding Speed | Arc Voltage | WFR | Welding Speed | WFR |
| Increase PD | ↓ | ↓ | ↑ | ↑ | ↓ | ↑ |
| Increase RH | ↑ | ↓ | ↓ | ↑ | ↓ | ↑ |
| Increase BW | ↓ | ↓ | ↑ | ↑ | ↓ | ↑ |
| Decrease variation of PD | ↓ | ↓ | ↓ | ↑ | ↑ | ? |
| Decrease variation of RH | ↑ | ↓ | ↓ | ↑ | ? | ? |
| Decrease variation of BW | ↓ | ↓ | ↓ | ↓ | ? | ? |

Figure 14:
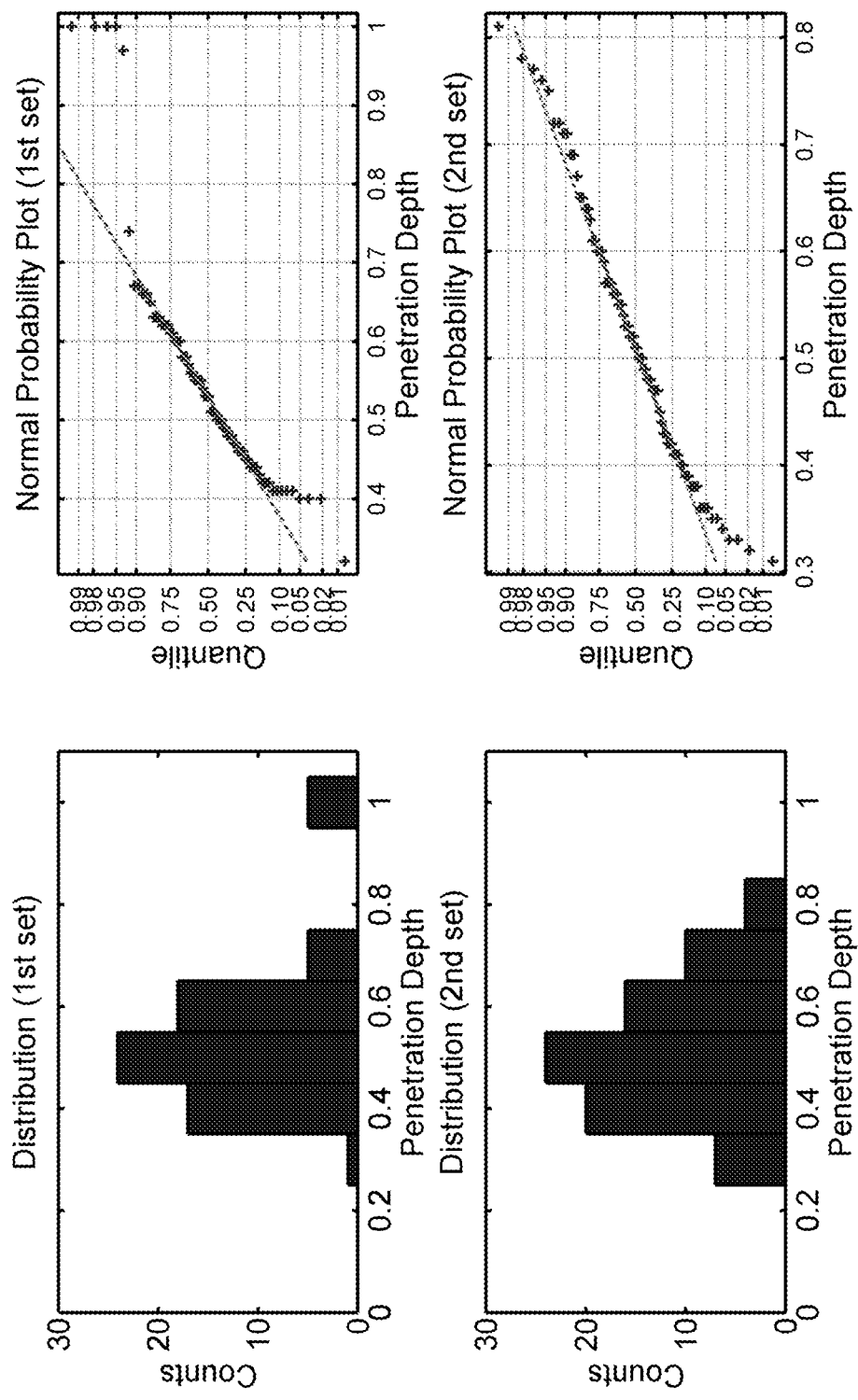
FIG. 14 depicts four histograms of PD and its normal probability plots for multiple sets of data.

The histogram of PD and its normal probability plots of both sets of data are shown in FIG. 14. The results show that the second set of data is more normally distributed than the first set of data, in which several data points have values of approximately one. These data points have large leverage and can easily bias the developed model(s). The range of PD of the second set of data is from 0.3 to 0.8, which is similar to the first set of data which range from 0.4 to 0.7. To build models with higher accuracy in the range where most of data points lie, therefore, simulations models can be developed using the second set of data as development data and then validated using the first set of data as validation data.

Signal Processing

As before, the SLS technique can be used to produce narrowband ultrasounds with every seven signals superimposed to produce the desired wavelengths. The desired wavelength can be determined by the pitch of the signals that are superimposed. If the signals from 7 line sources at a 2 mm interval are superimposed together, for example, then 2 mm will be the desired wavelength. In Example 4, for example, ten wavelengths from 1.75 mm to 4 mm in 0.25 mm increments are generated. The wave speed and frequency content of each of the Lamb wave modes at the desired wavelength can then be estimated from standard dispersion curves. The frequencies, phase velocities, and group velocities of $S_0$ and $A_0$ modes of the wavelengths of interest are listed in Table 7.

TABLE 7

Frequencies, Phase Velocities, and Group Velocities for $S_0$ and $A_0$ Modes

| | λ (mm) | 1.75 | 2.00 | 2.25 | 2.50 | 2.75 | 3.00 | 3.25 | 3.50 | 3.75 | 4.00 |
|---|---|---|---|---|---|---|---|---|---|---|---|
| S0 | f(MHz) | 1.75 | 1.56 | 1.41 | 1.30 | 1.22 | 1.15 | 1.10 | 1.06 | 1.02 | 0.99 |
| | Cp (m/s) | 3068.9 | 3116.7 | 3179.7 | 3257.6 | 3349.9 | 3455.1 | 3541.7 | 3696.8 | 3828.7 | 3964.7 |
| | Cg (m/s) | 2787.0 | 2675.6 | 2546.9 | 2407.5 | 2264.5 | 2125.7 | 1999.2 | 1892.9 | 1815.1 | 1773.8 |

TABLE 7-continued

Frequencies, Phase Velocities, and Group Velocities for $S_0$ and $A_0$ Modes

| λ (mm) | | 1.75 | 2.00 | 2.25 | 2.50 | 2.75 | 3.00 | 3.25 | 3.50 | 3.75 | 4.00 |
|---|---|---|---|---|---|---|---|---|---|---|---|
| A0 | f(MHz) | 1.69 | 1.47 | 1.29 | 1.15 | 1.04 | 0.94 | 0.86 | 0.79 | 0.72 | 0.67 |
|  | Cp (m/s) | 2956.1 | 2933.2 | 2907.3 | 2878.8 | 2848.3 | 2816.1 | 2782.7 | 2748.3 | 2713.1 | 2677.4 |
|  | Cg (m/s) | 3102.8 | 3129.1 | 3152.8 | 3174.1 | 3193.0 | 3209.6 | 3223.8 | 3235.6 | 3245.2 | 3252.4 |

As mentioned above, the broadband and dispersive laser ultrasound signals can first be simplified using the SLS technique. Compare, FIGS. 15a and 15b. In some embodiments, the method can further comprise applying k-ω domain filtering to filter out additional unwanted waves in the signals. The results of k-ω domain filtering are shown in FIGS. 16a-16c in which the X axis denotes frequency, the Y axis denotes wavenumber, and the darkness represents signal amplitude (the gray scale is reversed to give clarity to the graph).

FIG. 16(a) shows the original signals in k-ω domain, which is clearly broadband and dispersive in nature. FIG. 16(b) is identical to FIG. 16(a) with the theoretical solutions of Lamb wave modes of $S_0$, $A_0$, $S_1$, and $S_2$ modes overlapping the experimental data. The k-ω result of the signals after applying SLS technique for 3 mm wavelength is shown in FIG. 16(c). The image is basically symmetrical about the x axis. As before, the positive values of the wavenumber are for waves propagating with increasing distance of travel, and the negative values are for the waves with decreasing distance of travel.

The two bright stripes at the top center on approximately 0.94 MHz, 2094.4 rad/m and 1.15 MHz, 2094.4 rad/m and the third stripe at the bottom centers on approximately 0.94 MHz, −2094.4 rad/m. The wavenumber 2094.4 rad/m corresponds to wavelength 3 mm. The signals with negative wavenumbers can be filtered out, leaving only the signals with positive wavenumbers. The results can then be inversely transformed back into the space-time domain. See, FIG. 15c. Similarly, the signals containing positive wavenumbers can be filtered out, leaving only the signals with negative wavenumbers. These signals can then be inversely transformed back into the space-time domain. See, FIG. 15d.

In FIGS. 15c and 15d it is clear that the wave fronts with positive slopes and negative slopes have been separated successfully and the complexity of the signals is greatly reduced. Because the direct incident waves and reflection waves from the weld seam 1205a have increasing distance of travel as the source is moved away from the EMAT 1235, FIG. 15(c) contains all the necessary information for calculating reflection coefficients. By analyzing time-of-flight, the originations of wave components can be identified. Synthetic phase tuning technique can then be used to isolate a particular Lamb wave mode.

In some embodiments, for example, the signals can then be shifted in time. By shifting the signals properly in time, the desired mode can be isolated. FIG. 17a depicts the result for 3 mm $S_0$ mode and FIG. 17b depicts the result for 3 mm $A_0$ mode. In both cases, the incident and reflected waves from the weld can be identified by time-of-flight analysis. Thereafter, reflection coefficients can be calculated for both Lamb wave modes for each wavelength of interest. For each test location, 20 reflection coefficients can be calculated for ten wavelengths of two Lamb wave modes.

Analysis, Model Development, and Validation

In some embodiments, after reflection coefficients at each test location have been calculated and dimensions of the welds have been measured, models that correlate the reflection coefficients with the weld dimensions can be developed. Since no previous analytical formulations exist that describe the relationship between weld dimensions and reflection coefficients of Lamb waves, other mean must be employed. In some embodiments, regression analysis can be used here to develop one or more empirical models.

To begin the analysis, the assumption can be made that PD is a function of reflection coefficients. In regression analysis, a model with fewer independent variables is generally preferred as long as it can explain the data well. A model that overfits the data, for example, may give poor predictions. In some embodiments, therefore, a stepwise regression method and Corrected Akaike's Information Criterion (AICc) can be used to formulate the models with fewer significant predictors.

Stepwise Regression

In some embodiments, the method can further comprise stepwise regression. Stepwise regression is an automatic model selection algorithm that can identify statistically significant variables for a model. It adds or removes variables from the model by constantly evaluating the p-value of the variables. When using the stepwise regression, therefore, one can assign a threshold of p-value, or α. The p-value can be defined as a measure of how much evidence there is against a null hypothesis (i.e., in this case, that there is no correlation between PD and the reflection coefficients. In other words, if the p-value of a variable is smaller than α, it should be included in the model. When the p-value of a variable is larger than α, it can be excluded from the model. In addition, by varying α one can vary the number of variables in a prediction model. The stepwise regression procedures end up with the identification of a single "best" model.

Corrected Akaike's Information Criterion

In some embodiments, the method can further utilize Corrected Akaike's information criterion. AICc is an additional tool for model selection that measures how well a statistical model fits the data. AICc also penalizes models with large numbers of predictors, however, and thus determines the best size of the model when it reaches a minimum. AICc is defined in Eq. 10.

$$AICc = n \ln\left(\frac{SSE}{n}\right) + \frac{2np}{n-p-1} \tag{10}$$

where n is the number of observations, SSE is sum of square error, and p is the number of predictors in the model. In Eq. 10, n is given and remains constant for a model selection problem. As more predictors are added into the model, the first term decreases as SSE drops because of a better fit of the data but the second term increases as p increases. It will eventually reach the point when the decrease of the first term cannot compensate the increase of the second term in Eq. 10. The best size of the model is determined when AICc reaches a minimum.

Determination of Form of Regression Models

Regression analysis can be used to develop one or more empirical models to relate weld dimensions to reflection coefficients of Lamb waves. Since there is no theory that can be followed to determine the form of the regression models, polynomial regression models can be used. Polynomials can provide a good approximation of a function that is unknown or too complex such as, for example, a true curvilinear response. It should be noted, however, that polynomial models with higher than third order predictor variables present should be employed with special caution as these models can be highly erratic for interpolations and even small extrapolations.

In the current empirical model, the dependent variable is penetration depth and the independent variables can be the 20 reflection coefficients. The reflection coefficients can be named $A_0W_x$ and $S_0W_x$, which denote the reflection coefficients of $A_0$ and $S_0$ Lamb wave modes of the $x^{th}$ wavelength. The correspondence between x and the actual wavelength can be found in Table 8.

TABLE 8

Variables used in Regression Model

| x | Wavelength (mm) | Mode: A0 | Mode: S0 |
|---|---|---|---|
| 1 | 1.75 | A0W1 | S0W1 |
| 2 | 2.00 | A0W2 | S0W2 |
| 3 | 2.25 | A0W3 | S0W3 |
| 4 | 2.50 | A0W4 | S0W4 |
| 5 | 2.75 | A0W5 | S0W5 |
| 6 | 3.00 | A0W6 | S0W6 |
| 7 | 3.25 | A0W7 | S0W7 |
| 8 | 3.50 | A0W8 | S0W8 |
| 9 | 3.75 | A0W9 | S0W9 |
| 10 | 4.00 | A0W10 | S0W10 |

In some embodiments, a cubic polynomial with second order cross-product interaction terms can be chosen for the regression analysis. Cubic polynomials have 251 coefficients to be determined. These coefficients can include one intercept, 20 coefficients for linear terms, 20 coefficients for quadratic terms, 20 coefficients for cubic terms, and 190 coefficients for the second order cross-product interaction terms. Of course, most of these parameters can be omitted because they are statistically insignificant.

Model Development

In some embodiments, stepwise regression can first be used to find a suitable model. A very lenient criterion such as, for example, $\alpha=0.2$ can be used to include more than necessary predictors in the model with the understanding that, in this configuration, the model may overfit the data. As mentioned above, the p-value is a measure of how much evidence there is to reject the null hypothesis. In this case, the null hypothesis is that the variable under evaluation is not significant. The 21 terms selected and their indices are shown in the first two columns of Table 9.

TABLE 9

Summary of model development and validation for PD

| Index | Term | p | Indices of terms in model | AICc | $R^2$ | RMSE |
|---|---|---|---|---|---|---|
| 1 | A0W2 | 1 | 7 | −317.942 | 0.7980 | 0.1252 |
| 2 | A0W5 | 2 | 7, 18 | −338.43 | 0.8400 | 0.1118 |
| 3 | A0W7 | 3 | 7, 17, 18 | −365.773 | 0.8665 | 0.1094 |
| 4 | A0W8 | 4 | 1, 6, 17, 19 | −378.317 | 0.8765 | 0.1110 |
| 5 | S0W1 | 5 | 1, 6, 11, 14, 16 | −402.061 | 0.8888 | 0.1108 |
| 6 | S0W4 | 6 | 1, 6, 7, 11, 14, 16 | −411.761 | 0.8959 | 0.1080 |
| 7 | S0W6 | 7 | 5, 6, 7, 10, 16, 18, 19 | −416.513 | 0.9017 | 0.1067 |
| 8 | A0W1*A0W2 | 8 | 2, 7, 10, 11, 12, 17, 19, 21 | −420.596 | 0.9073 | 0.1043 |
| 9 | A0W1*A0W10 | 9 | 2, 5, 7, 10, 11, 12, 16, 17, 19 | −430.719 | 0.9138 | 0.0983 |
| 10 | A0W2*A0W5 | 10 | 2, 4, 5, 7, 10, 11, 12, 16, 17, 19 | −435.98 | 0.9188 | 0.0941 |
| 11 | A0W2*S0W4 | 11 | 4, 5, 6, 7, 9, 10, 16, 17, 18, 19, 21 | −434.091 | 0.9236 | 0.0952 |
| 12 | A0W2*S0W6 | 12 | 5, 7, 8, 9, 10, 11, 12, 13, 17, 19, 20, 21 | −434.404 | 0.9283 | 0.0914 |
| 13 | A0W5*A0W10 | 13 | 2, 5, 7, 8, 9, 10, 11, 12, 13, 16, 17, 19, 20 | −421.64 | 0.9297 | 0.0955 |
| 14 | A0W7*A0W10 | 14 | 4, 5, 6, 7, 8, 9, 10, 13, 16, 17, 18, 19, 20, 21 | −424.204 | 0.9305 | 0.0976 |
| 15 | A0W9*S0W4 | 15 | 4, 5, 6, 7, 8, 9, 10, 13, 14, 16, 17, 18, 19, 20, 21 | −423.206 | 0.9309 | 0.1029 |
| 16 | S0W1*S0W5 | 16 | 2, 4, 5, 7, 8, 9, 10, 11, 12, 13, 15, 16, 17, 19, 20, 21 | −421.91 | 0.9313 | 0.0912 |
| 17 | S0W4*S0W5 | 17 | 2, 4, 5, 7, 8, 9, 10, 11, 12, 13, 15, 16, 17, 18, 19, 20, 21 | −419.627 | 0.9315 | 0.0966 |
| 18 | S0W5*S0W6 | 18 | 2, 4, 5, 7, 8, 9, 10, 11, 12, 13, 14, 15, 16, 17, 18, 19, 20, 21 | −416.686 | 0.9317 | 0.0948 |
| 19 | S0W7*S0W8 | 19 | 2, 4, 5, 6, 7, 8, 9, 10, 11, 12, 13, 14, 15, 16, 17, 18, 19, 20, 21 | −413.325 | 0.9319 | 0.0998 |
| 20 | A0W9^3 | 20 | 2, 3, 4, 5, 6, 7, 8, 9, 10, 11, 12, 13, 14, 15, 16, 17, 18, 19, 20, 21 | −408.807 | 0.9319 | 0.0973 |
| 21 | S0W5^3 | 21 | ALL | −403.877 | 0.9320 | 0.1006 |

Statistical software such as, for example and not limitation, JMP 8.0 can then be used to calculate AICc values for all the possible regression models that can be constructed using these 21 terms. The analysis can also identify the model that gives the lowest AICc value for the corresponding number of predictors, p, used. The third column in Table 9 denotes the number of predictors, p, included in the model. The forth column shows the terms corresponding to p which are used in the model to obtain the lowest AICc values. The fifth column shows the AICc values. The sixth column shows the coefficient of determination ("$R^2$") values and the seventh column shows the root mean square errors (RMSE), discussed below, when these models are validated with the validation data.

Figure 18:
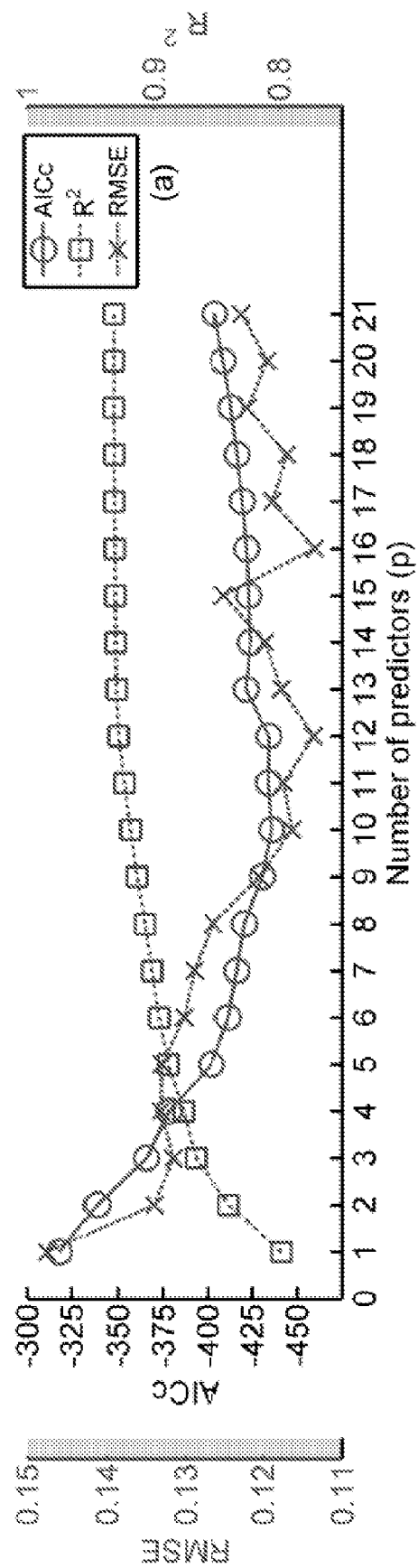
FIG. 18 is a graph depicting the relationship between Corrected Akaike's Information Criterion and the coefficient of determination with respect to the number of predictors in a model.

For p=2, for example, the model that is constructed using term 7 and term 18, or equivalently $S_0W_6$ and $S_0W_5*S_0W_6$, gives the lowest AICc value as −338.43 and $R^2$ as 0.84. The relationship between AICc and $R^2$ values with respect to p, or the number of predictors in the model, are shown in FIG. 18. The solid line depicts AICc and the dashed line depicts $R^2$. For each p, the AICc value is the smallest value among all the possible values obtained from the models with the same number of predictors. As expected, the $R^2$ value increases as p increases since the addition of predictors tends to reduce the error of the model. On the other hand, in this example, the AICc value reaches a minimum when p is around 12.

Model Validation

TABLE 10

Coefficients of the Prediction Model

| Term | Estimate |
| --- | --- |
| Intercept | 1.18219921 |
| S0W1 | 0.66770091 |
| S0W6 | −2.6862286 |
| A0W1*A0W2 | 2.18494892 |
| A0W1*A0W10 | −2.6532654 |

TABLE 10-continued

Coefficients of the Prediction Model

| Term | Estimate |
| --- | --- |
| A0W2*A0W5 | −2.4432716 |
| A0W2*S0W4 | −7.5774344 |
| A0W2*S0W6 | 4.8703709 |
| A0W5*A0W10 | 1.98233193 |
| S0W4*S0W5 | 6.18720021 |
| S0W7*S0W8 | −0.2492727 |
| A0W9^3 | 0.55037 |
| S0W5^3 | −2.500456 |

To find the model with highest accuracy, the 21 models in Table 9 can be built, and error analysis and model validation can be carried out using validation data. The RMSE with respect to p is also shown in FIG. 18. As shown, the RMSE reaches a minimum value, 0.0912, when p=16 and the second minimum value, 0.0914, is reached when p=12. Because the values are significantly the same, the model with p=12 should be chosen since it has fewer predictors. The coefficients of the prediction model are shown in Table 10.

Figure 19A:
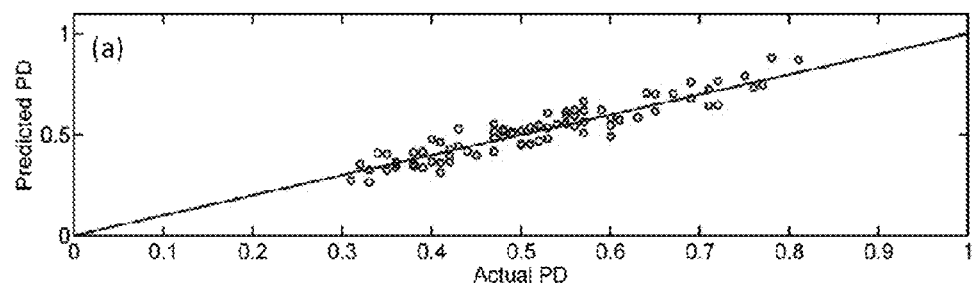
FIGS. 19a-19d depict the relationship between predicted and measured outcomes from penetration depth using embodiments of the present invention.
Figure 19B:
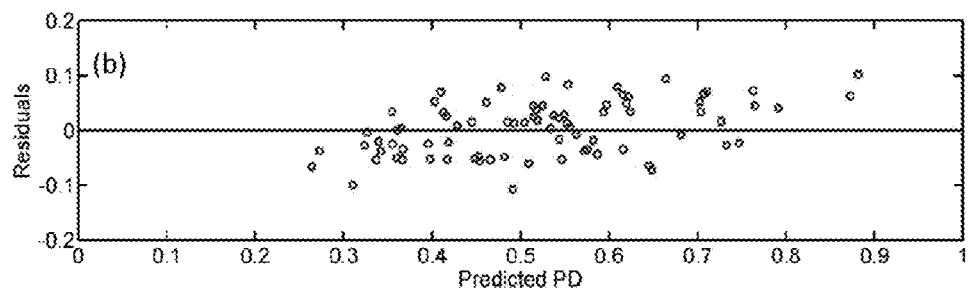
Figure 19C:
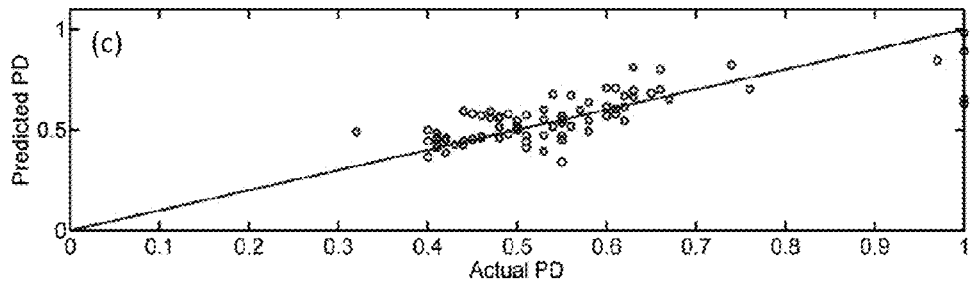
Figure 19D:
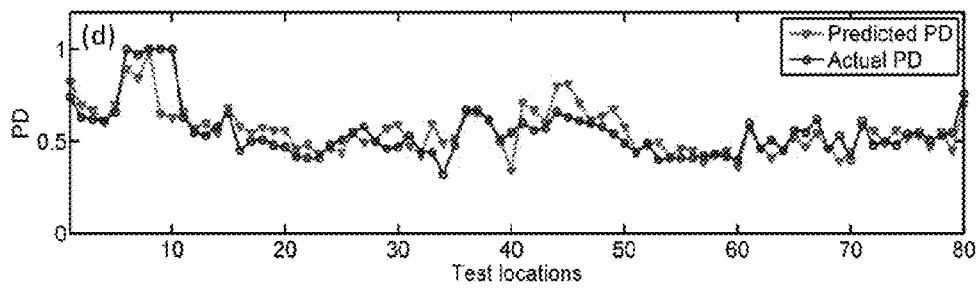

The relationship between actual PD and predicted PD from the model development data is shown in FIG. 19a. The $R^2$ value of this model is 0.9312. The residual plot is shown in FIG. 19b. As shown, most of the errors are within ±0.1 and no systematic errors are observed, which indicates adequacy of the model. FIG. 19c shows the relationship between actual PD and predicted PD from the model validation data, while FIG. 19d shows actual and predicted PD versus experiment runs. As shown, correlation between the predicted PD and the actual PD is excellent.

Additional Model Development and Validation with Addition of RH and BW as Predictors In some embodiments, a laser profilometer can used to measure the reinforcement height ("RH") and bead width ("BW") of a butt weld. The same model development procedure discussed previously can then be applied to build the prediction model for PD with RH and BW as predictors. The addition of known terms enables a model with a smaller number of predictors. The sixteen terms selected by the stepwise regression using the development data and α=0.2 are shown in the first two columns in Table 11.

TABLE 11

Summary of Model Development and Validation for PD

| Index | Term | p | Indices of terms in model | AICc | $R^2$ | RMSE |
| --- | --- | --- | --- | --- | --- | --- |
| 1 | BW*A0W9 | 1 | 7 | −271.59 | 0.8766 | 0.1043 |
| 2 | BW*S0W4 | 2 | 3, 7 | −301.95 | 0.9174 | 0.1008 |
| 3 | BW*S0W7 | 3 | 3, 4, 8 | −323.90 | 0.9388 | 0.0856 |
| 4 | RH*A0W6 | 4 | 3, 4, 7, 8 | −336.39 | 0.9490 | 0.0904 |
| 5 | RH*A0W10 | 5 | 3, 4, 7, 8, 14 | −340.79 | 0.9531 | 0.0839 |
| 6 | RH*S0W3 | 6 | 3, 4, 7, 8, 9, 14 | −352.09 | 0.9605 | 0.0804 |
| 7 | RH*S0W9 | 7 | 3, 4, 7, 8, 9, 12, 14 | −357.11 | 0.9640 | 0.0774 |
| 8 | RH*S0W10 | 8 | 2, 3, 4, 7, 8, 9, 12, 14 | −362.06 | 0.9672 | 0.0811 |
| 9 | A0W1*S0W6 | 9 | 2, 3, 4, 7, 8, 9, 12, 14, 16 | −360.87 | 0.9697 | 0.0790 |
| 10 | A0W2*A0W7 | 10 | 3, 4, 7, 8, 9, 10, 11, 13, 15, 16 | −358.76 | 0.9718 | 0.0837 |
| 11 | A0W2*S0W3 | 11 | 2, 4, 7, 8, 9, 10, 11, 12, 13, 15, 16 | −359.29 | 0.9745 | 0.0833 |
| 12 | A0W3*A0W10 | 12 | 2, 3, 4, 7, 8, 9, 10, 11, 12, 13, 15, 16 | −361.32 | 0.9775 | 0.0798 |
| 13 | A0W6*S0W3 | 13 | 2, 3, 4, 6, 7, 8, 9, 10, 11, 12, 13, 15, 16 | −358.88 | 0.9790 | 0.0793 |
| 14 | A0W6*S0W10 | 14 | 2, 3, 4, 6, 7, 8, 9, 10, 11, 12, 13, 14, 15, 16 | −355.41 | 0.9801 | 0.0842 |
| 15 | A0W7*S0W4 | 15 | 2, 3, 4, 5, 6, 7, 8, 9, 10, 11, 12, 13, 14, 15, 16 | −353.32 | 0.9816 | 0.0850 |
| 16 | S0W4^3 | 16 | ALL | −347.41 | 0.9821 | 0.0837 |

TABLE 12

Coefficients of the Prediction Model for PD

| Term | Estimate |
| --- | --- |
| Intercept | 1.18219921 |
| S0W1 | 0.66770091 |
| S0W6 | −2.6862286 |
| A0W1*A0W2 | 2.18494892 |
| A0W1*A0W10 | −2.6532654 |
| A0W2*A0W5 | −2.4432716 |
| A0W2*S0W4 | −7.5774344 |
| A0W2*S0W6 | 4.8703709 |
| A0W5*A0W10 | 1.98233193 |
| S0W4*S0W5 | 6.18720021 |
| S0W7*S0W8 | −0.2492727 |
| A0W9^3 | 0.55037 |
| S0W5^3 | −2.500456 |

These sixteen models can be built with increasing number of predictors as described in the earlier section. These models can then be validated by the validation data and the RMSE values of each model are listed in Table 12 as well. The AICc reaches the local minimum −362.06 when p=8. The $R^2$ values increase with p as expected. The RMSE follows the trend of AICc and reaches the minimum value, 0.0774, when p=7. In this case, the best model is not the one indicated by the AICc value.

Compared to the results in Table 12, it clearly shows that with the addition of RH and BW as predictors, the model we developed can predict PD more accurately with fewer predictors. Therefore, if RH and BW measurements are available, it is better to include them into the prediction model. The coefficients of the prediction model are shown in Table 13. The results also show that the AICc value cannot always determine the prediction model. In a preferred embodiment, therefore, it can be desirable to validate the model by using another set of data and then calculating the RMSE values to determine the best model.

TABLE 13

Summary of Model Development and Validation for PD

| Index | Term | p | Indices of terms in model | AICc | $R^2$ | RMSE |
|---|---|---|---|---|---|---|
| 1 | BW*A0W9 | 1 | 7 | −271.59 | 0.8766 | 0.1043 |
| 2 | BW*S0W4 | 2 | 3, 7 | −301.95 | 0.9174 | 0.1008 |
| 3 | BW*S0W7 | 3 | 3, 4, 8 | −323.90 | 0.9388 | 0.0856 |
| 4 | RH*A0W6 | 4 | 3, 4, 7, 8 | −336.39 | 0.9490 | 0.0904 |
| 5 | RH*A0W10 | 5 | 3, 4, 7, 8, 14 | −340.79 | 0.9531 | 0.0839 |
| 6 | RH*S0W3 | 6 | 3, 4, 7, 8, 9, 14 | −352.09 | 0.9605 | 0.0804 |
| 7 | RH*S0W9 | 7 | 3, 4, 7, 8, 9, 12, 14 | −357.11 | 0.9640 | 0.0774 |
| 8 | RH*S0W10 | 8 | 2, 3, 4, 7, 8, 9, 12, 14 | −362.06 | 0.9672 | 0.0811 |
| 9 | A0W1*S0W6 | 9 | 2, 3, 4, 7, 8, 9, 12, 14, 16 | −360.87 | 0.9697 | 0.0790 |
| 10 | A0W2*A0W7 | 10 | 3, 4, 7, 8, 9, 10, 11, 13, 15, 16 | −358.76 | 0.9718 | 0.0837 |
| 11 | A0W2*S0W3 | 11 | 2, 4, 7, 8, 9, 10, 11, 12, 13, 15, 16 | −359.29 | 0.9745 | 0.0833 |
| 12 | A0W3*A0W10 | 12 | 2, 3, 4, 7, 8, 9, 10, 11, 12, 13, 15, 16 | −361.32 | 0.9775 | 0.0798 |
| 13 | A0W6*S0W3 | 13 | 2, 3, 4, 6, 7, 8, 9, 10, 11, 12, 13, 15, 16 | −358.88 | 0.9790 | 0.0793 |
| 14 | A0W6*S0W10 | 14 | 2, 3, 4, 6, 7, 8, 9, 10, 11, 12, 13, 14, 15, 16 | −355.41 | 0.9801 | 0.0842 |
| 15 | A0W7*S0W4 | 15 | 2, 3, 4, 5, 6, 7, 8, 9, 10, 11, 12, 13, 14, 15, 16 | −353.52 | 0.9816 | 0.0850 |
| 16 | S0W4^3 | 16 | ALL | −347.41 | 0.9821 | 0.0837 |

In some embodiments, it may be desirable to analyze more models that have the second or third lowest AICc values for each p, or the number of predictors. If all these models can predict PDs equally well, then another criterion may be introduced to decide which model is the best. For example, a model that uses reflection coefficients of fewer wavelengths is better than the one that uses those of more wavelengths because this will save both experimental and signal processing time.

It is possible that any model developed may be unable to accurately predict weld behavior when the variables (e.g., weld dimensions or material type) are disparate from those used in model development. In other words, the models may hold true for materials within a certain range of thicknesses or for different types of mild steel, but not stainless steel. In industry, however, the majority of materials used in the welding processes in a manufacturing plant are typically fixed. In the automobile industry, for example, the type and the thickness of the steel used for a certain part in a car model is typically identical. This is, after all, the heart of mass production.

In addition, one manufacturing line is usually dedicated to one type of material, one thickness, and one type of welding process. A welding robot arm, for example, performs one task in one cell and the samples are transported to the next cell for another task. The process is simple and is, in general, repeated without little or no changes. As a result, the data driven approach disclosed herein is very efficient, effective, and valuable.

Embodiments of the present invention, therefore, relate to a system and method that provide an effective means for measuring various weld parameters, including penetration depth (PDs) of welds in thin plates. The superimposed laser source (SLS) technique can effectively generate narrowband Lamb waves in thin plates while retaining the noncontact benefits of laser generation. A signal processing procedure can combines wavenumber-frequency (k-ω) domain filtering and synthetic phase tuning (SPT) techniques to further reduce the complexity of Lamb wave signals and facilitate the calculation of reflection coefficients of different wavelengths and wave modes.

In some embodiments, regression analysis can be used to develop prediction models that relate the reflection coefficients of Lamb waves to the PDs in the butt welds in thin plates. The method for the model development can include stepwise regression and Corrected Akaike's Information Criterion (AICc). The method can optimize the number of predictors used in the prediction models. Reinforcement height (RH) and bead width (BW) dimensions can be included in the prediction model to reduce the number of predictors required and to improve the accuracy of the model.

The simulation and experimental results have shown strong agreement, and have demonstrated the potential of this technique in, for example and not limitation, non-destructive testing and analysis of welds in thin plates. While several possible embodiments are disclosed above, including on-line real-time NDT in industrial settings, embodiments of the present invention are not so limited. For instance, while several possible configurations have been disclosed, other suitable materials and combinations of materials could be selected without departing from the spirit of embodiments of the invention. In addition, the location and configuration used for various features and components of embodiments of the present invention can be varied according to a particular material, weld size, or weld setting that requires a slight variation due to, for example, surrounding machinery (e.g., on an assembly line) or other space and/or power constraints. Such changes are intended to be embraced within the scope of the invention.

The specific configurations, choice of materials, and the size and shape of various elements can be varied according to particular design specifications or constraints requiring a device, system, or method constructed according to the principles of the invention. Such changes are intended to be embraced within the scope of the invention. The presently disclosed embodiments, therefore, are considered in all respects to be illustrative and not restrictive. The scope of the invention is indicated by the appended claims, rather than the foregoing description, and all changes that come within the meaning and range of equivalents thereof are intended to be embraced therein.

We claim:

1. A method for non-destructively analyzing a weld in a sample comprising:
   (1) activating a pulsed, concentrated energy source to create ultrasonic waves in the sample;
   (2) receiving the ultrasound waves with an ultrasound receiver;
   (3) storing the signal generated by the ultrasound receiver on a computer readable medium;
   (4) moving the sample a first predetermined distance;
   repeating steps 1-4 until the sample has moved a second predetermined distance and a plurality of signals generated by the ultrasound receiver have been stored on the computer readable medium;
   creating a model correlating the plurality of signals generated by the ultrasound receiver with empirical data for the sample;
   retrieving the signals stored on the computer readable medium;
   superimposing the signals that correspond to a first wavelength to create a first artificial narrowband ultrasound source; and
   storing the first artificial narrowband ultrasound source on the computer readable medium.

2. The method of claim 1 further comprising:
   retrieving the first artificial narrowband ultrasound source from the computer readable medium;
   reducing the complexity of the first artificial narrowband ultrasound source using a two-dimensional Fourier transform, producing a second narrowband ultrasound source; and
   storing the second narrowband ultrasound source on the computer readable medium.

3. The method of claim 1 further comprising:
   retrieving the first artificial narrowband ultrasound source from the computer readable medium;
   reducing the complexity of the first narrowband ultrasound source using a complex Morlet mother wavelet, producing a third narrowband ultrasound source; and
   storing the third narrowband ultrasound source on a computer readable medium.

4. The method of claim 1 wherein the first predetermined distance is smaller than the first wavelength.

5. The method of claim 1, wherein the model is created using regression analysis.

6. The method of claim 5, wherein the regression analysis further comprises using Corrected Akaike's Information Criterion.

7. The method of claim 6 further comprising:
   measuring a reinforcement height of the weld; and
   including reinforcement height as a predictor to be included in the regression analysis.

8. The method of claim 6 further comprising:
   measuring a bead width of the weld; and
   including bead width as a predictor to be included in the regression analysis.

9. The method of claim 6 further comprising:
   measuring one or more dimensions of the weld using a laser profilometer.

10. A system for non-destructively analyzing a weld in a sample comprising:
    a concentrated energy source for creating localized heating in the sample to cause ultrasonic waves;
    an ultrasound receiver for receiving the ultrasonic waves;
    a linear stage for moving the sample at a predetermined step interval;
    a computer readable medium for storing one or more signals generated by the ultrasound receiver;
    a model for correlating the one or more signals generated by the ultrasound receiver to empirical data; and
    a processor configured to perform the following:
    retrieving the signals stored on the computer readable medium;
    superimposing the signals that correspond to a first wavelength to create a first artificial narrowband ultrasound source; and
    storing the first artificial narrowband ultrasound source on the computer readable medium.

11. The system of claim 10, wherein the concentrated energy source is a pulse width laser.

12. The system of claim 10, wherein the concentrated energy source is an electromagnetic acoustic transducer ("EMAT").

13. The system of claim 10, wherein the ultrasound receiver is an EMAT.

14. The system of claim 11 further comprising a cylindrical lens for converting the concentrated energy from the pulsed width laser to a line source narrowband ultrasound.

15. The system of claim 10 further comprising a computer processor for superimposing the one or more signals generated by the ultrasound receiver to reduce the complexity of the signals.

16. The system of claim 15, wherein the computer processor further reduces the complexity of the signals using a complex Morlet mother wavelet.

17. The system of claim 16, wherein the computer processor further reduces the complexity of the signals using a two-dimensional Fourier transform.

18. The system of claim 10, wherein the empirical data for the model comprises cutcheck data.

19. The system of claim 10, wherein the model is created using regression analysis.

* * * * *